US012637477B2

(12) United States Patent
Bonomi

(10) Patent No.: US 12,637,477 B2
(45) Date of Patent: May 26, 2026

(54) SYNTHESIS PROCESS OF AMIDE DERIVATIVES OF HYDROXYPENICILLANIC ACID

(71) Applicant: Paolo Bonomi, Maisons-Alfort (FR)

(72) Inventor: Paolo Bonomi, Maisons-Alfort (FR)

( * ) Notice: Subject to any disclaimer, the term of this patent is extended or adjusted under 35 U.S.C. 154(b) by 361 days.

(21) Appl. No.: 18/267,890

(22) PCT Filed: Dec. 15, 2021

(86) PCT No.: PCT/IB2021/061766

§ 371 (c)(1),
(2) Date: Jun. 16, 2023

(87) PCT Pub. No.: WO2022/130238

PCT Pub. Date: Jun. 23, 2022

(65) Prior Publication Data

US 2024/0059708 A1 Feb. 22, 2024

(30) Foreign Application Priority Data

Dec. 16, 2020 (IT) ........................ 102020000031070

(51) Int. Cl.

| | |
|---|---|
| ***C07D 499/08*** | (2006.01) |
| ***C07D 499/40*** | (2006.01) |
| ***C07D 513/04*** | (2006.01) |

(52) U.S. Cl.

CPC ......... *C07D 499/08* (2013.01); *C07D 499/40* (2013.01); *C07D 513/04* (2013.01)

(58) Field of Classification Search

CPC ... C07D 499/08; C07D 499/40; C07D 513/04

See application file for complete search history.

(56) References Cited

FOREIGN PATENT DOCUMENTS

| | | | |
|---|---|---|---|
| EP | 3626721 | A2 | 3/2020 |
| WO | 2017153892 | A1 | 9/2017 |

OTHER PUBLICATIONS

Fanni, Stefano: "International Search Report and Written Opinion of the International Searching Authority for International Application No. PCT/IB2021/061766", European Patent Office, Apr. 13, 2022.

Liu Chun-Jing et al, "Synthesis of new penicillin derivatives as drug-like molecules for biological screening", Chinese Chemical Letters, Elsevier, Amsterdam, NL, vol. 26, No. 1, Sep. 16, 2014 (Sep. 16, 2014), p. 113-117, XP029132720 DOI: 10.1016/J.CCLET.2014.09.008 ISSN:1001-8417 ; cited in the application scheme 2.

Perkin J C S et al, "Transformations of Penicillins : New Methods of Formation and Reactions of 6,6-Disubstituted Penams and 7,7-Disubstituted Cephems", Jan. 1, 1976 (Jan. 1, 1976), Retrieved from the Internet: URL:https://pubs.rsc.org/en/content/articlepdf/1976/p1/p19760001918?page=search XP055832474 ; [retrieved on Aug. 17, 2021] scheme 4.

*Primary Examiner* — Susanna Moore

(74) *Attorney, Agent, or Firm* — Florek & Endres PLLC

(57) ABSTRACT

A process for the synthesis of amide derivatives of 8-hydroxypenillic acid is described, more specifically starting from amide derivatives of the 6-aminopenicillanic nucleus protected as tert-butylcarbamate.

9 Claims, 21 Drawing Sheets

(IIB)

trzadcH, 88 %

Structure of trzadcH (IIB)

Avibactam

Avibactam containing a triazole unit (3*S*,7*R*,7a*R*)-3-((3-azidopropyl)carbamoyl)-2,2-dimethyl-5-oxohexahydroimidazo[5,1-*b*]thiazole-7-carboxylic acid

Composto (IIA)

Composto (IB)

Composto (IIB)

Composto (IIC)

SYNTHESIS PROCESS OF AMIDE DERIVATIVES OF HYDROXYPENICILLANIC ACID

The present invention relates to a new process for the synthesis of amide derivatives of 8-hydroxypenillic acid, more specifically starting from amide derivatives of the 6-aminopenicillanic nucleus protected as tert-butylcarbamate.

Sep. 3, 1928 can certainly be counted as being one of the most important days in human history. Thanks, in fact, to the discovery of Penicillin G by the doctor, biologist and pharmacologist Alexander Fleming, mankind passed from the era of plagues, characterized by an average life expectancy of 47 years and millions of deaths due to pandemic plagues, to the era of chronic diseases with an average life expectancy of 70 years[(1), (2)].

In the following years, with the industrial production of Penicillins, Cephalosporins and other types of antibiotics, the fight against bacterial infections seemed to have been overcome. The microbes (bacteria, fungi, mycobacteria and parasites), however, almost immediately showed the ability to defend themselves against these new drugs by developing different resistance mechanisms[(3)]. The indiscriminate use of antibiotics, especially in the past, has also led to the formation of new bacteria resistant not only to a specific antibiotic, but also to different classes of antibiotics.

Some bacteria such as *Staphylococcus aureus*, resistant to the most powerful antibiotics, were isolated in as early as 1950[(4), (5)].

The race for finding new antibiotics, however, seemed relentless even though other therapies, such as vaccines, were beginning to be used successfully in certain situations.

Unfortunately, even today, the resistance developed by bacteria to antibiotics remains one of the most disturbing and serious threats to human health. There are in fact strains of virtually "immortal" microbes, for which there is no remedy[(6), (7)].

In 2017 in Europe, the cost in terms of human lives and in economic terms, caused by resistance to antibiotics by microorganisms was estimated at about 33,000 deaths and €1.5 billion euro (https://ec.europa.eu/health/amr/antimicrobial-resistance_en).

According to the American Centre for Disease Control and Prevention (CDC), each year, about 2.8 million people in America are infected with bacteria that are resistant to conventional antibiotics, of which about 35,000 die. (https://www.cdc.gov/drugresistance/index.html).

Unfortunately, the trend is destined to grow so dramatically that, in the absence of new effective remedies, the possibility of returning to an era of (preantibiotic) plagues cannot be excluded. After all, as reported on the World Health Organization website, in 2030, due to antibiotic resistance, 24 million people will risk living in a state of extreme poverty, and as of 2050 there could be about 10 million deaths every year (https://www.who/int/news-room/detail/29-04-2019-new-report-calls-for-urgent-action-to-avert-antimicrobial-resistance-crisis). Furthermore, at least 700,000 people are already dying every year from drug-resistant diseases.

Resistance to antibiotics by bacteria and fungi and, more generally, by microorganisms, therefore represents an ever-growing problem and certainly constitutes one of the most important challenges that humans will have to face in the years to come (https://www.who.int/news-room/fact-sheets/detail/antibiotic-resistance).

The search for new antibacterial drugs is therefore currently of vital importance together with the possibility of synthesizing new molecules starting from the modification and study of old drugs[(8), (9)].

One of the most urgent needs is undoubtedly that of developing new drugs against bacterial defenses such as, for example, bacterial β-lactamases. These are enzymes capable of destroying antibiotics and allowing bacteria to survive becoming resistant and "immortal"[(10)].

In particular, the pharmaceutical world is considering the idea of re-evaluating and modifying old molecules for producing new drugs[(11)].

AntibioticDB, for example, is a recent database of antibiotics in use or in the testing phase and of antibiotics whose study has been abandoned, also extremely useful for studying the development of new products.[(12)].

For this reason, the search for innovative synthesis processes that lead to new or already known intermediates/precursors which, in turn, can then lead to obtaining new active molecules, is also extremely important.

New synthesis routes, for example, starting from beta-lactam nuclei such as the 6-aminopenicillanic nucleus (6-APA) and the 7-aminocephalosporanic nucleus (7-ACA), are described in WO2017153892 and in Italian patent application Nr. 102018000007656. These synthesis routes are based on the modification of the carboxyl function of said nuclei, protected as tert-butylcarbamates in the amino position (N-Boc), which allows a modulation of the pharmacological activity of these nuclei to be investigated.

Through these synthesis routes, it is in fact possible to effectively carry out an important diversification at the level of the carboxyl group for the 6-APA and 7-ACA nuclei, protected on the amino function as tert-butyl carbamates, thus making it possible to obtain precursors of new molecules that can also be used as "building blocks" for new products, or used for functionalizing nanoparticles in order to implement and enhance the pharmacological properties of antibiotics themselves. In particular, the cycloaddition reaction between an organic azide and a terminal alkyne is widely used for this purpose[(13)].

In order to further proceed towards the differentiation of these building blocks to create new entities with a possible pharmacological action, a further step is necessary, however, which consists in the removal of the tert-butyl group from the amino group to thus allow a subsequent functionalization of the amino group.

In the above-mentioned documents WO2017153892 and IT102018000007656, the penicillanic and cephalosporanic nuclei had been protected as tert-butyl carbamates on the amino position with the specific aim of being able to modify the carboxyl group to then free the amino group and effect new modifications.

One of the most widespread and described methods in literature for releasing the protected amino group such as tert-butyl carbamate is to use trifluoroacetic acid as a chemical agent (http://www.commonorganicchemistry.com/Rxn_Pages/Boc_Protection/Boc_Protection_TFA_Mech.htm).

This deprotection has been extensively described in literature on cephalosporanic acid derivatives as shown in FIG. 1.

U.S. Pat. No. 4,788,185 in fact describes the deprotection reaction with trifluoroacetic acid or other reagents to obtain the elimination of the carbamate and the release of the amino group, with preservation of the β-lactam structure (FIG. 1).

In U.S. Pat. Nos. 4,244,951, 4,364,957 and 4,419,284 deprotection reactions of some derivatives of penicillins protected as paranitrobenzyloxycarbonylamino (FIG. 33)

under acid conditions for acetic acid, in the presence of palladium on carbon, in a hydrogen atmosphere, to give the corresponding penicillan product with the deprotected amino group with a yield of 23% (U.S. Pat. No. 4,244,951). Following the deprotection reaction described in these documents (acid environment and hydrogen atmosphere) deprotection alone takes place without any rearrangement.

Consequently, in the case of the 6-APA penicillanic nucleus and relative derivatives, no deprotection process of the amino function protected as tert-butyl carbamate is yet known. The problem of the deprotection of the amino function, protected as tert-butyl carbamate consequently has no solution in the state of the art in the case of the 6-APA penicillan nucleus and in particular in the case of its primary or secondary amide derivatives.

The objective of the present invention is therefore to identify a rapid, simple and quantitative process for removing the tert-butyl group from the amino group of derivatives of the 6-amino-penicillanic nucleus (N-Boc protected), overcoming the drawbacks of the prior art.

DESCRIPTION OF THE INVENTION

The present invention therefore relates to a process for the synthesis of derivatives of 8-hydroxypenillic acid starting from amide derivatives of the N-Boc-protected 6 amino-penicillanic nucleus, wherein the compound having formula (I)

(I)

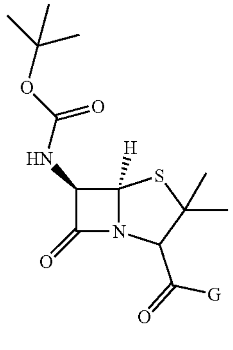

with G equal to a $NR_1R_2$ group wherein $R_1$ and $R_2$ are selected from hydrogen and a linear alkyl chain having from 2 to 5 carbon atoms, preferably 2 or 3 carbon atoms, with an azide group, a propargyl group or a triazole group functionalized with a saccharide or relative derivative, preferably peracetylated glucose, galactose, hexoses, pentoses or oligosaccharides suitably derivatized with a terminal alkyne group, more preferably peracetylated glucose, wherein $R_1$ and $R_2$ are not simultaneously equal to hydrogen, is subjected to a deprotection reaction carried out in the presence of an excess of trifluroacetic acid (TFA) in a polar solvent, preferably selected from methylene chloride (DCM), chloroform ($CHCl_3$) or tetrahydrofuran (THF), preferably methylene chloride (DCM) or chloroform ($CHCl_3$), at a temperature ranging from 0° C. to room temperature, for a period of time ranging from 5 minutes to 2 hours, obtaining the compound having formula (II)

II

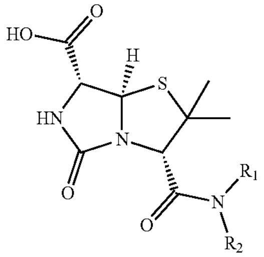

wherein $R_1$ and $R_2$ have the meanings previously indicated.

This reaction surprisingly allows the quantitative removal of the tert-butyl group to be rapidly and easily obtained, freeing the amino group and filling the gaps of the known art.

In particular, this process removes the tert-butyl group of the amino group of derivatives of the 6 amino-penicillan nucleus (N-Boc protected), wherein the carboxyl group has been converted into secondary or tertiary amides as described in Italian patent application Nr. 102018000007656, surprisingly leading to the formation of new derivatives of 8-hydroxypenillic acid.

Furthermore, with reference to the synthesis of secondary and tertiary amides, an improvement in reaction yield has been obtained with respect to the method disclosed in the above Italian patent application, using as an activating agent 1-[Bis(dimethylamino)methylene]-1H-1,2,3-triazolo[4,5-b] pyridinium 3-oxide hexafluorophosphate (HATU) in dichloromethane, in the presence of triethylamine (TEA) or diisopropylethylenamine (DIPEA). Using these activating agents, especially HATU, it was possible to isolate the amidation product with a yield between 40 and 60%.

In the deprotection process, i.e., in eliminating the tert-butyloxycarbonyl group $(CH_3)_3COC{=}O$, the loss of the tert-butyl group $(CH_3)_3CO$ alone and the retention of the carboxyl group $C{=}O$ were surprisingly obtained, giving, in fact, new amide derivatives of 8-hydroxypenillic acid, as described in detail hereunder.

Figure 2:
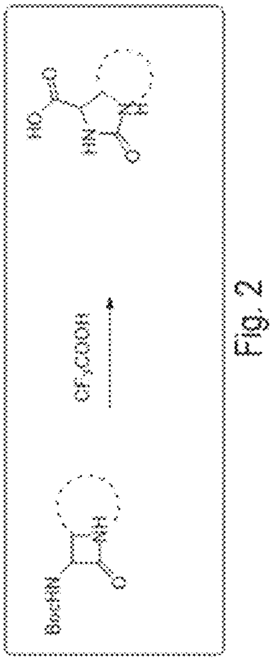
FIG. 2 shows the deprotection according to the process of the present invention.

Using trifluoroacetic acid as reagent for the N-Boc deprotection of secondary and tertiary amide derivatives of the penicillanic nucleus (6-APA) protected on the amino group as tert-butylcarbamate, the applicant unexpectedly obtained a quantitative N-Boc deprotection of the starting products, associated with an equally quantitative transformation of the β-lactam nucleus (the azetidine-2-one nucleus) into a 5-nucleus such as that of 2-imidazolidinone as shown in FIG. 2.

Figure 3:
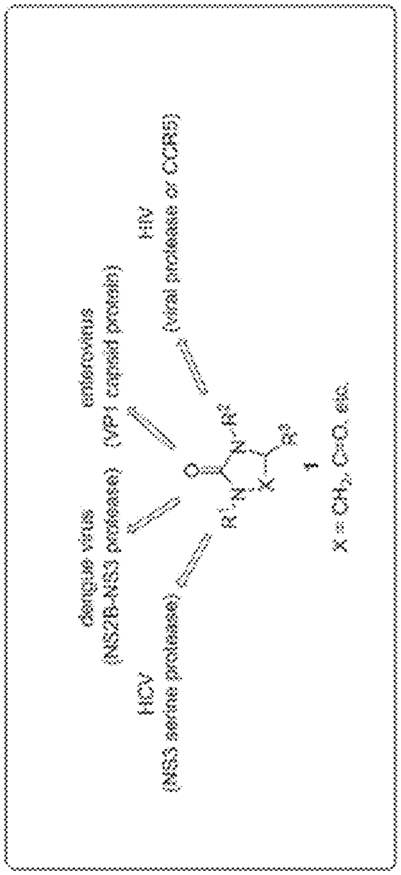
FIG. 3 shows examples of molecules containing the 2-imidazolidinone nucleus.

It should be noted that the 2-imidazolidinone nucleus is present in numerous molecules with different pharmacological activities such as antiviral drugs (especially for HIV), pesticides and antipsychotics[(14)] (FIG. 3).

Figure 1:
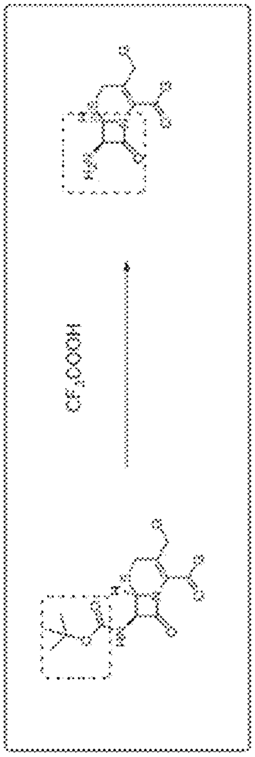
FIG. 1 shows the deprotection using trifluoroacetic acid as a chemical agent described in literature on cephalosporanic acid derivatives according to the prior art.
Figure 4:
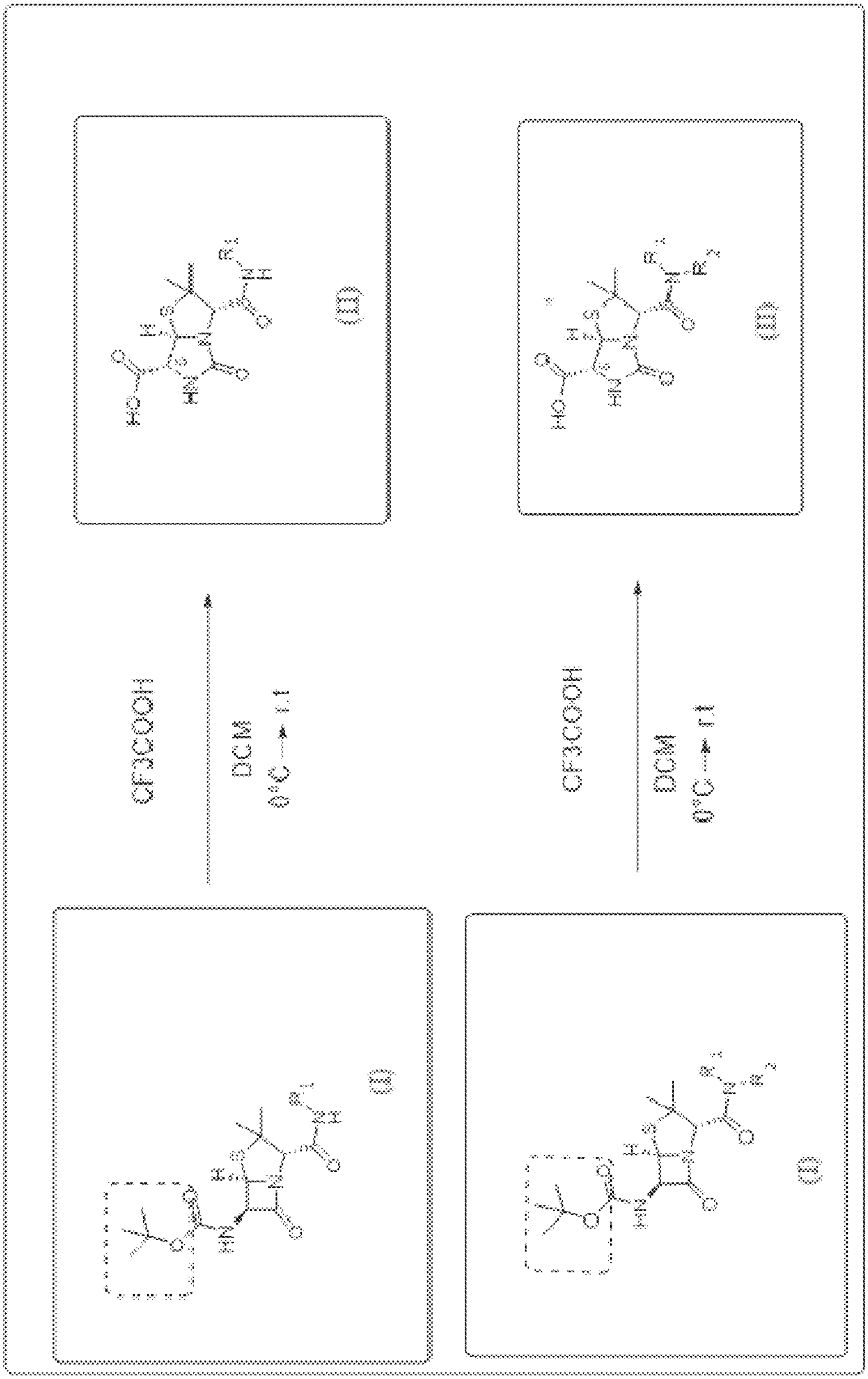
FIG. 4 shows the structural rearrangement of the beta-lactam nucleus (four-ring) to a 5-ring (2-imidazolidinone), giving rise to the formation of a molecule containing two 5-cycles condensed together according to the process of the present invention.
Figure 33:
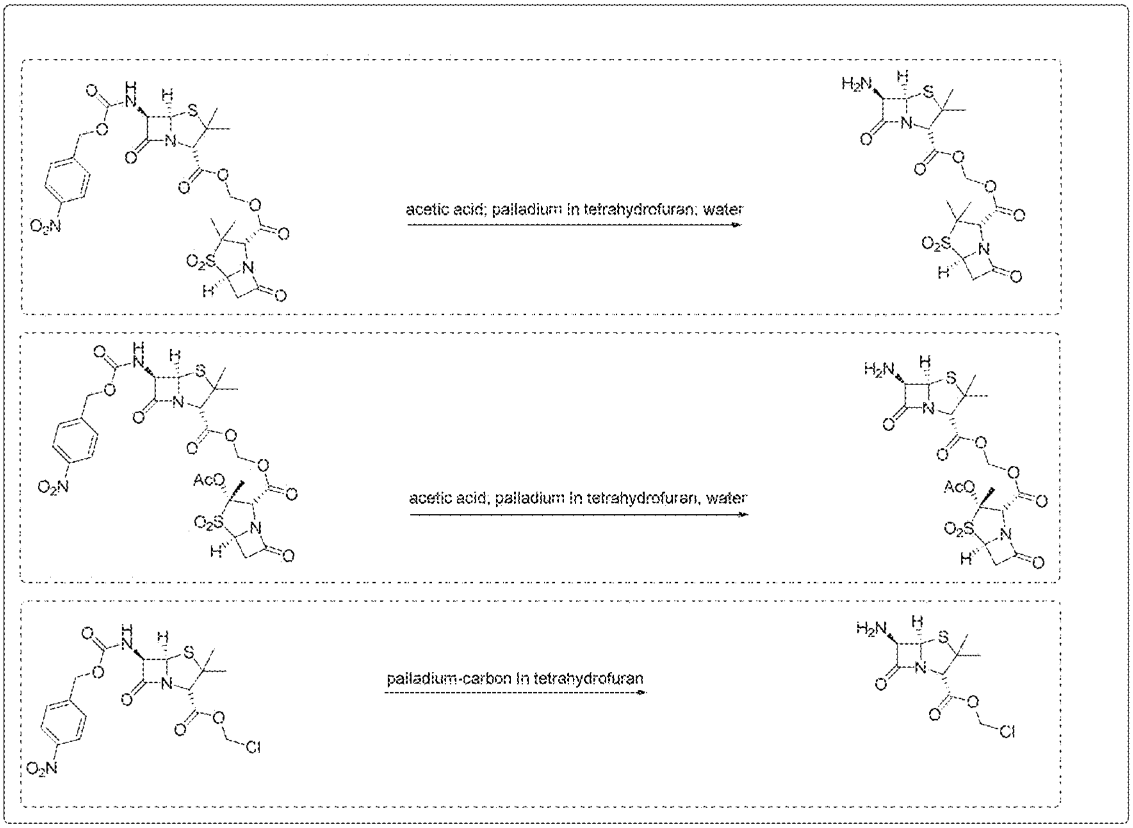
FIG. 33 shows deprotection reactions of some derivatives of penicillins protected as paranitrobenzyloxycarbonylamino according to the prior art.

Consequently, equally surprisingly and in contrast with what is known in literature with reference to the release of the amino group by removal of the tert-butyloxycarbonyl group from 7-ACA derivatives (FIG. 1), and the 4-nitrobenzyloxycarbonyl group from penicillan derivatives (FIG. 33), the process according to the present invention also leads to said structural rearrangement of the beta-lactam nucleus (four-ring) to a 5-ring (2-imidazolidinone), giving rise to the formation of a molecule containing two 5-cycles condensed together (FIG. 4).

In particular, the substrates taken into consideration for this deprotection reaction, i.e. the compounds having formula (I) are secondary or tertiary amide derivatives of the 6-APA nucleus, protected on the amino group as tert-butyl carbamate.

Examples of these substrates, i.e. preferred compounds having formula (I), are selected from the compounds (IA), (IB), (IC), (ID) and (IE) indicated hereunder:

(IA)

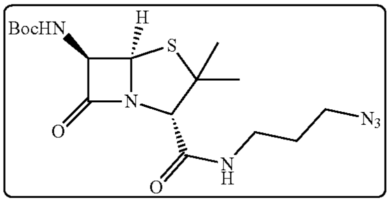

(IB)

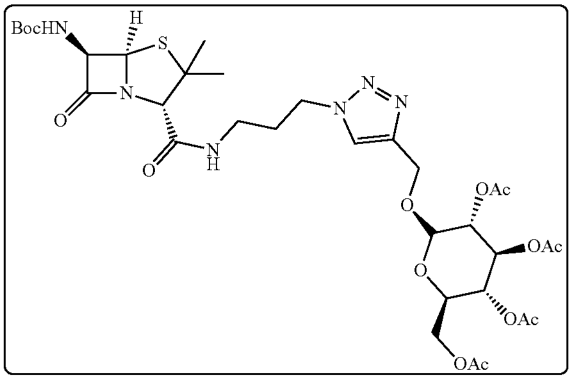

(IC)

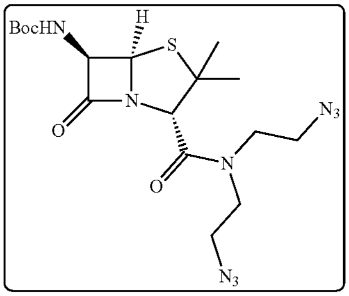

-continued (ID)

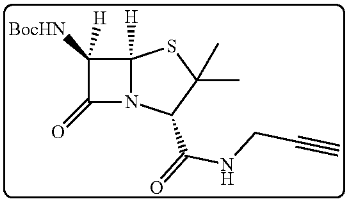

(IE)

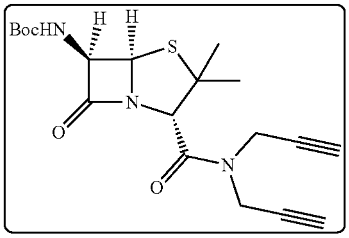

In the process according to the present invention, an excess of trifluroacetic acid (TFA) preferably refers to a quantity of trifluoroacetic acid which ranges from 50 to 100 mmoles in a molar ratio with respect to the compound having formula (I).

The term room temperature refers to a value of 25° C. (plus/minus 2° C.).

The present invention also relates to amide derivatives of 8-hydroxypenillic acid having general formula (II) having the following structural formulae (IIA), (IIB), (IIC), (IID) and (IIE) indicated hereunder:

(IIA)

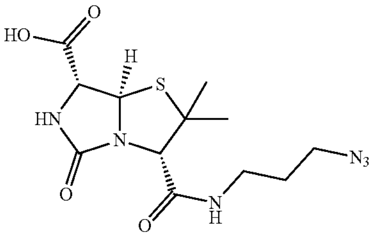

(IIB)

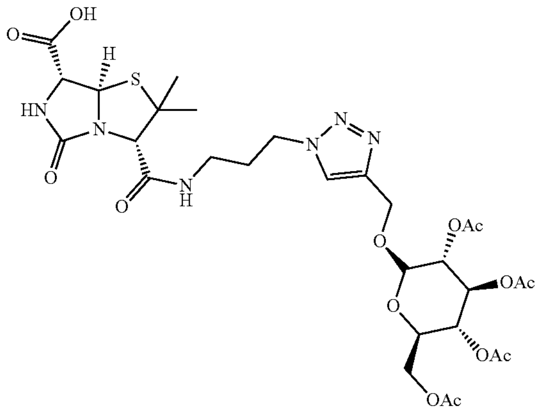

-continued (IIC)

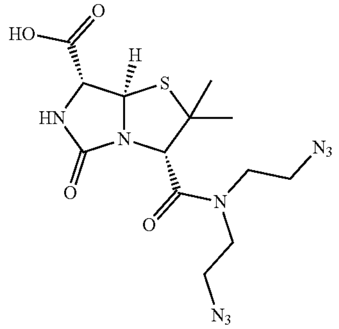

(IID)

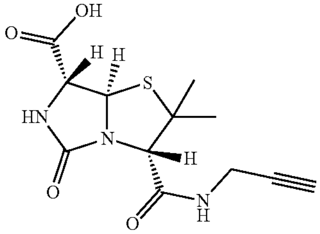

(IIE)

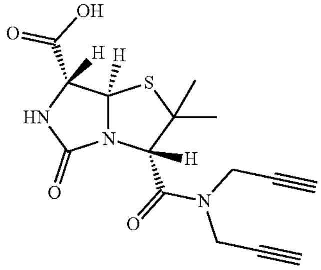 [SMILES: C#CCN(CC#C)C(=O)[C@@H]1N2C(=O)N[C@H](C(=O)O)[C@H]2SC1(C)C]

Figure 5:
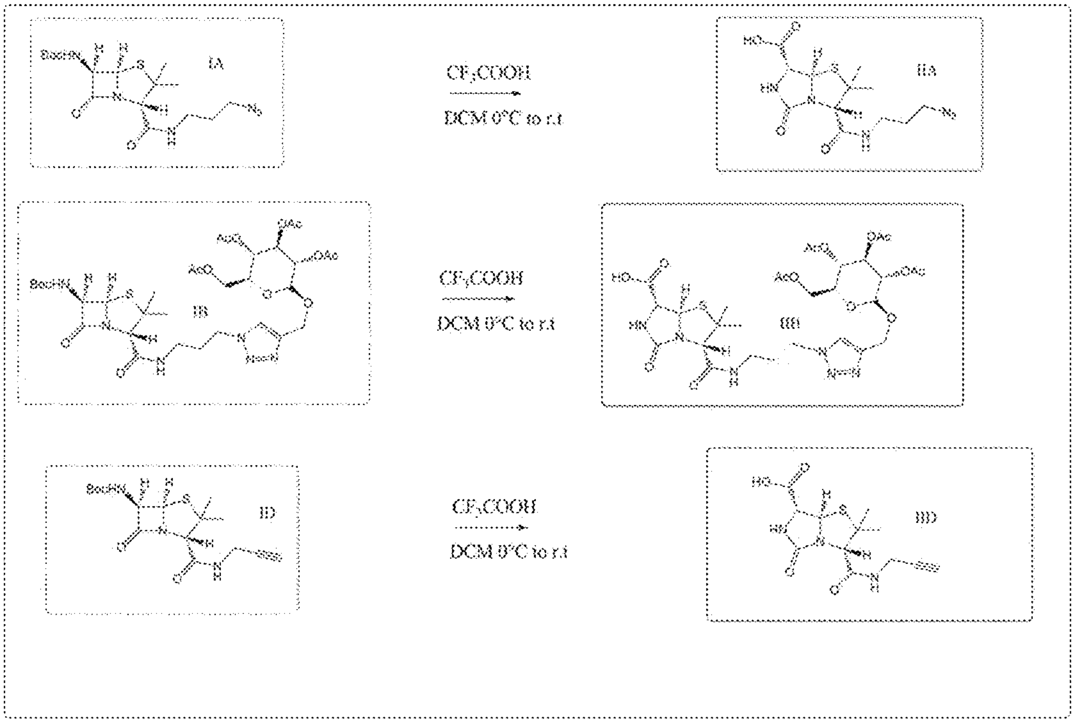
FIG. 5 shows some examples of the process according to the present invention starting from secondary amides.

FIG. 5 shows some examples of the process according to the present invention starting from secondary amides, wherein the starting product (IA), with an alkyl group with 3 carbon atoms and an azide group, leads to the formation of compound (IIA), whereas the starting product (IB), having an alkyl group with 3 carbon atoms and a triazole functionalized with a peracetylated glucose, leads to the formation of compound (IIB).

In the same way the starting product (ID), with an alkyl group with 3 carbon atoms and a terminal alkyne group, leads to the formation of compound (IID). In the state of the art the starting product (ID) has never been disclosed. In literature, however, it is disclosed the amide derivative containing the propargyl group of benzylpenicillin.

Figure 6:
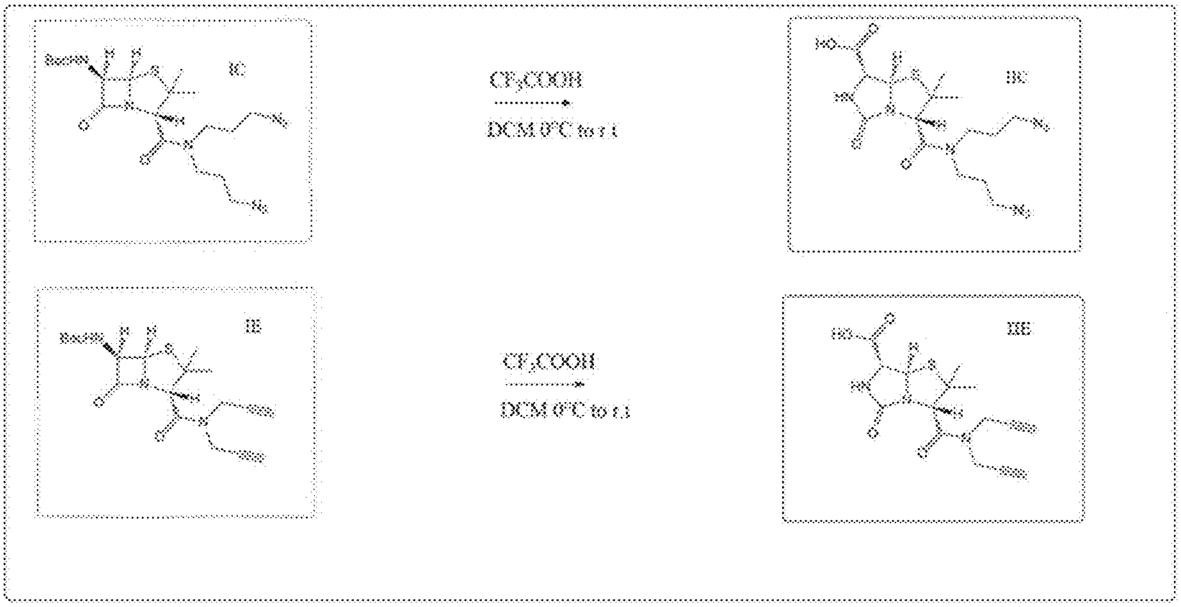
FIG. 6 shows some examples of the process according to the present invention starting from tertiary amides.

Again, by way of example of the process according to the present invention, in FIG. 6, starting from tertiary amides, the starting product (IC), with two alkyl groups having two carbon atoms and two azide groups, leads to the formation of compound (IIC). Using the same synthesis method, product (IE), namely the tertiary amide derivative containing two propargyl groups, leads to the formation of compound (IIE).

The basic structure of these molecules is already known in literature with the name of "8-hydroxypenillic acid" or 3,3-dimethyl-8-oxo-4-thia-1,7-diazabicyclo [3.3.0] octane-2,6-dicarboxyl acid. The first work describing this dates back to 1961[(15)], later confirmed in 2014 in WO2014/71283A1.

There are extremely significant differences, however, between the basic structure and the processes described in literature and the object of the present invention, with reference to the starting products having formula (I), the products obtained from formula (II) and the process itself.

Figure 7:
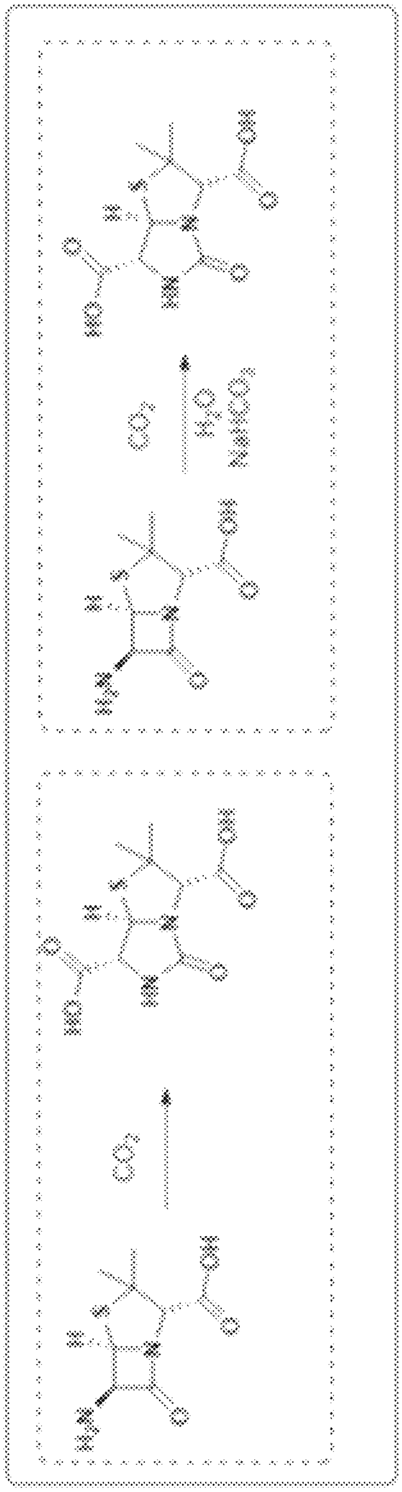
FIG. 7 shows that the reaction of the free amino group with CO2 causes the decomposition of the penicillanic nucleus to give the disodium salt of 8-hydroxy penillic acid.

In the works reported in literature, in fact, the 6-APA nucleus (6-amino penicillanic) with the free amino group (and therefore not protected as tert-butyl carbamate) and with the free carboxyl group (and therefore not transformed into secondary and/or tertiary amide) is treated in a neutral or basic environment in the presence of $CO_2$ (carbon dioxide). The reaction of the free amino group with $CO_2$ causes the decomposition of the penicillanic nucleus to give the disodium salt of 8-hydroxypenillic acid (FIG. 7). In order for this reaction to take place, it is essential for the amino group to be free to bind the $CO_2$ present in the reaction environment and then cause the opening and rearrangement of the ring. This reaction is obviously not reproducible on substrates such as those having formula (I) as the amino group is protected as tert-butylcarbamate and is therefore not available for binding $CO_2$. Similarly, the final products are necessarily different as they do not include a secondary or tertiary amide group.

This type of rearrangement had also been described enzymatically by a class C β-lactamase from *Enterobacter cloacae* P99 in 1996[(16)].

Also in this case, there is no evidence that this reaction can take place on the substrates having formula (I), both because the amino group is protected as tert-butyl carbamate, and also because the carboxyl group is sterically hindered by the presence of a more or less bulky amide group.

Figure 8:
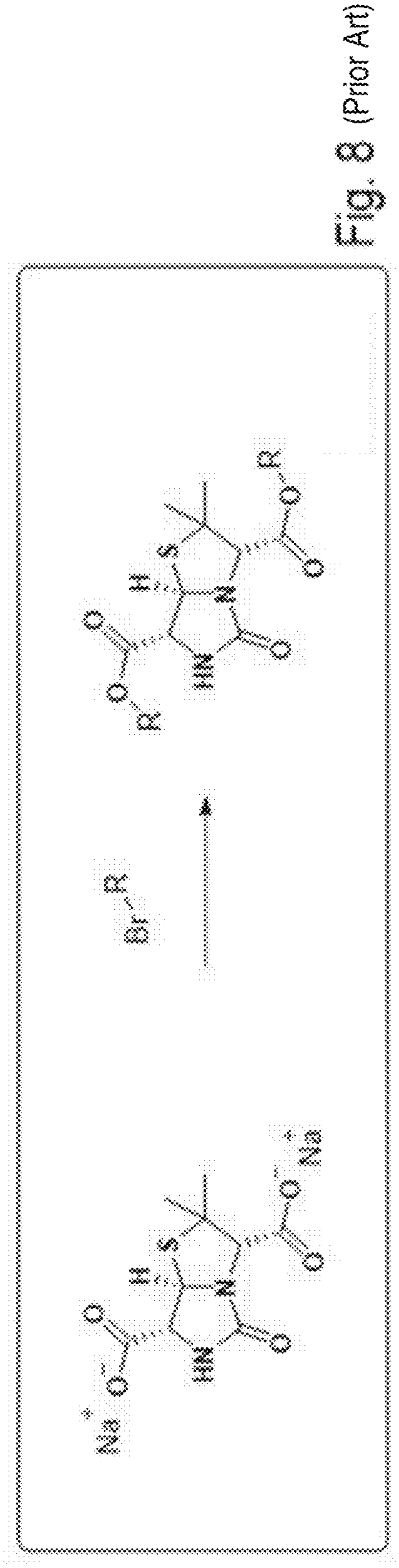
FIG. 8 shows that the disodium salt of 8-hydroxy penillic acid was used in literature for obtaining diester derivatives according to the prior art.

Furthermore, in literature, as indicated in FIG. 8, the disodium salt of 8-hydroxypenillic acid was subsequently used for obtaining diester derivatives[(17)] which have various pharmacological properties: they can be used, for example, as inhibitors of the TAAR1 receptor (which regulates the neurotransmission of dopamine at the level of the central nervous system) and can therefore be used for psychiatric or neurodegenerative diseases, or they can be used for increasing the survival of "human induced stem cells".

With the process indicated in FIG. 8 and described in literature, molecules of interest from a pharmacological point of view are thus obtained, but it is evident that only di-esters or di-amides functionalized with the same substituents can be prepared through this synthesis route. Consequently, only symmetrical molecules can be obtained.

The process according to the present invention, on the contrary, allows derivatives of 8-hydroxypenillic acid to be synthesized with an amide group (secondary or tertiary containing azides or functionalized triazole groups) and a free carboxyl group which can therefore be functionalized at will, both as ester, and as amide, and also following other possible reduction reactions. By means of the process according to the present invention, asymmetric compounds (having different substituents) or symmetrical compounds (having identical substituents) can evidently be obtained according to interest. This result obviously cannot be obtained by means of the process indicated in FIG. 8.

Figure 9:
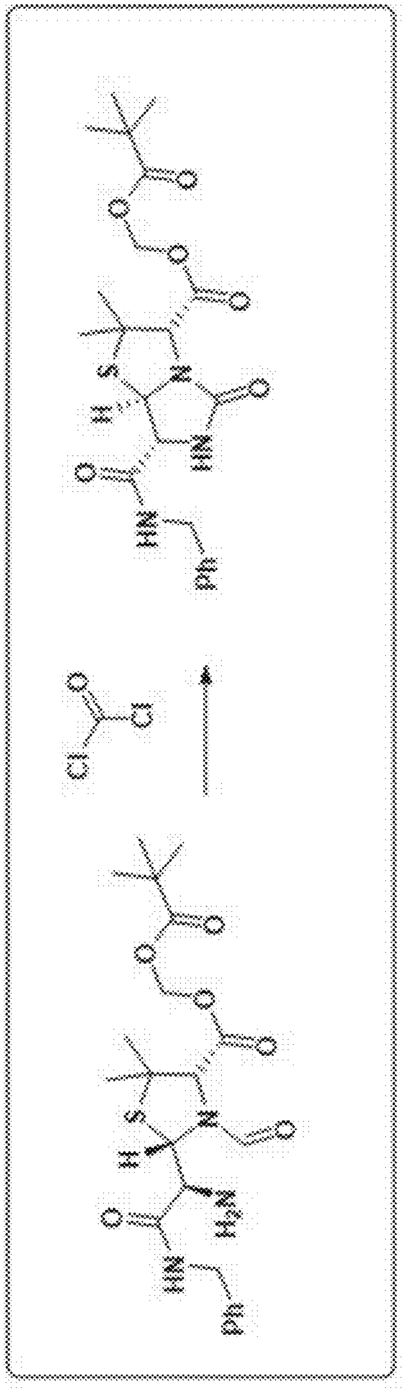
FIG. 9 shows that derivatives of 8-hydroxy penillic acid have been obtained using highly toxic compounds such as phosgene according to the prior art.

Further derivatives of 8-hydroxypenillic acid, described in[(18)], have been obtained using highly toxic compounds such as phosgene, as shown in FIG. 9.

As already specified therefore, a process for obtaining derivatives of 8-hydroxypenillic acid having a secondary or tertiary amide group and a free carboxyl function in position 6 (as shown in FIG. 4), i.e. compounds having formula (II), is not known in literature, said carboxyl function being ready for being subsequently functionalized in an ester or amide or reduced to alcohol or oxidized to aldehyde.

The process according to the present invention therefore surprisingly allows:

1) the tert-butyl group $(CH_3)_3CO$ to be removed, using trifluoroacetic acid, maintaining the carboxyl group C═O with a rearrangement of the β-lactam ring in a cyclic urea to give the reaction product having formula (II) with quantitative yields as observed by NMR analysis, not as yet described in literature;
2) new amide derivatives of 8-hydroxypenillic acid and not described in literature, to be obtained.

The amide derivatives of 8-hydroxypenillic acid with the carboxyl group in free 6 position (see FIG. 4), i.e. unprotected as ester or amide, having formula (II) are in fact surprisingly obtained simply and rapidly, without the use of toxic and dangerous substances. The compounds having formula (II) are intermediates/precursors ready for subsequent modifications and for obtaining new antibiotic derivatives with pharmacological activities possibly also extended to fungi and other microbes.

Both the synthesis process and the products obtained having formula (II), never described in literature, are compounds of considerable interest both as compounds in themselves having a biological activity, and as precursors for new derivatives of high pharmacological interest.

As previously indicated, compounds containing the 2-imidazolidinone group can have an antiviral (anti-HIV) activity [(19)] or, as in the case of satranidazole, an anti-parasitic (anthelmintic) activity https://pubchem.ncbi.nlm.nih.gov/compound/Satranidazole. Imidrapril is an antihypertensive https://en.wikipedia.org/wiki/Imidapril, whereas azlocillin (antibiotic) is a derivative of penicillin containing a substituent consisting of a 2-imidazolidinone ring[(20)].

These intermediates or precursors having formula (II) can therefore be functionalized in very different ways by means of suitable reactions to obtain new molecules.

As previously specified, numerous molecules with a pharmacological activity such as antiviral, anti-cancer, antibacterial drugs and antifungicides containing a cyclic urea such as 2-imidazolidinone, are described in literature[(21)].

Figure 10:
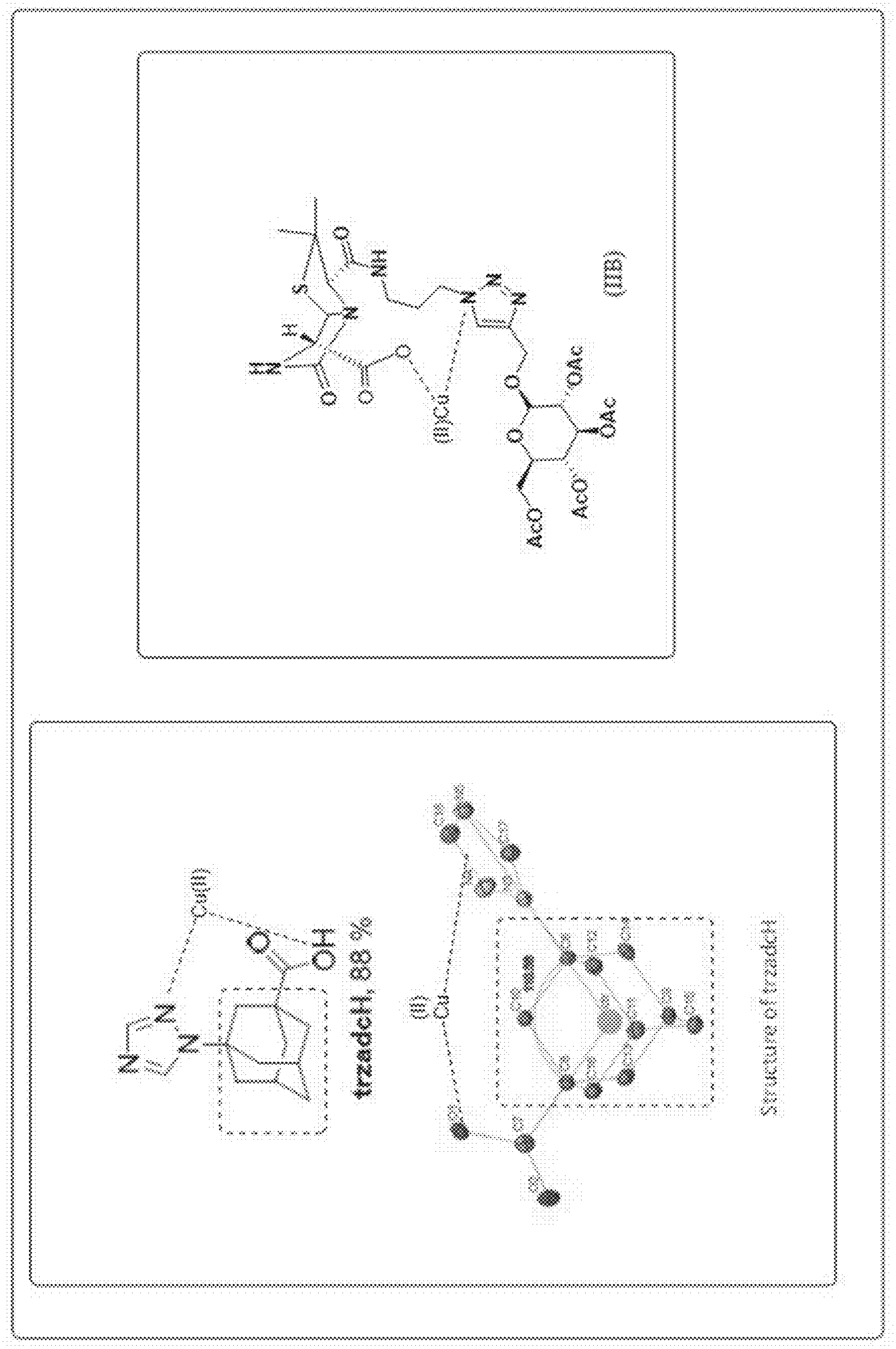
FIG. 10 shows a coordination effect on the preparation of coordination polymers using ligands consisting of an adamantane nucleus containing a carboxyl group at one end and a triazole group at the other end according to the prior art.

Furthermore, the molecules having formula (II) obtained with the process according to the present invention, allow an intramolecular interaction between the carboxyl group and one or two triazole groups present in the molecule itself. The carboxyl group and the triazole groups, although separated in space by the penicillan nucleus, are however both spatially directed downwards with respect to the cyclic system and are therefore oriented in such a way as to have a possible synergistic coordination effect. This interaction is extremely important for reinforcing the coordination of divalent metal ions such as Copper (II), Zinc (II), Magnesium (II) and Nickel (II). A similar coordination effect has been described in a work centered on the preparation of coordination polymers using ligands consisting of an adamantane nucleus containing a carboxyl group at one end and a triazole group at the other end[(22)] (FIG. 10).

It is, in fact, important to remember the importance of metal ions in the virulence of pathogenic bacteria and the destructive effect of chelating molecules on said pathogenic bacteria.

In order to understand the importance of the process according to the present invention and the products thus obtained, it should be remembered that one of the major causes at the origin of the phenomenon of bacterial resistance to antibiotics, lies in the bacterial enzymes known as β-lactamase. More than 4,000 are known.

The most dangerous are known as metal β-lactamase as they require a zinc (II) ion for destroying antibiotics and it has been demonstrated that chelating agents are essential for the inhibition of these bacterial enzymes[(23)]. It should be noted that today there are fewer than 30 known inhibitors of bacterial β-lactamase and there is therefore a great need for finding new molecules and new chemical strategies for having access to new products with an inhibitory activity towards these bacterial enzymes.

The products obtained with the process according to the present invention consequently have all the physico-chemical characteristics necessary for possessing a pharmacological action of considerable interest, especially as antimicrobials and inhibitors of bacterial β-lactamases, but also as antiviral and anticancer agents[(24)].

In this respect, it seems important to indicate some similarities between the products according to the present invention and one of the most important and effective bacterial β-lactamase inhibitors, having a non β-lactamase structure, i.e. avibactam and a recent derivative thereof described in WO2019/122438, 2019, A1 and in[(25)].

Avibactam contains a cyclic urea in a condensed five ring in a structure known as "diazabicyclooctane" and WO'438 specifies how the insertion of triazole rings, in structures of this type, allows their inhibitory properties to be modulated.

Figure 11:
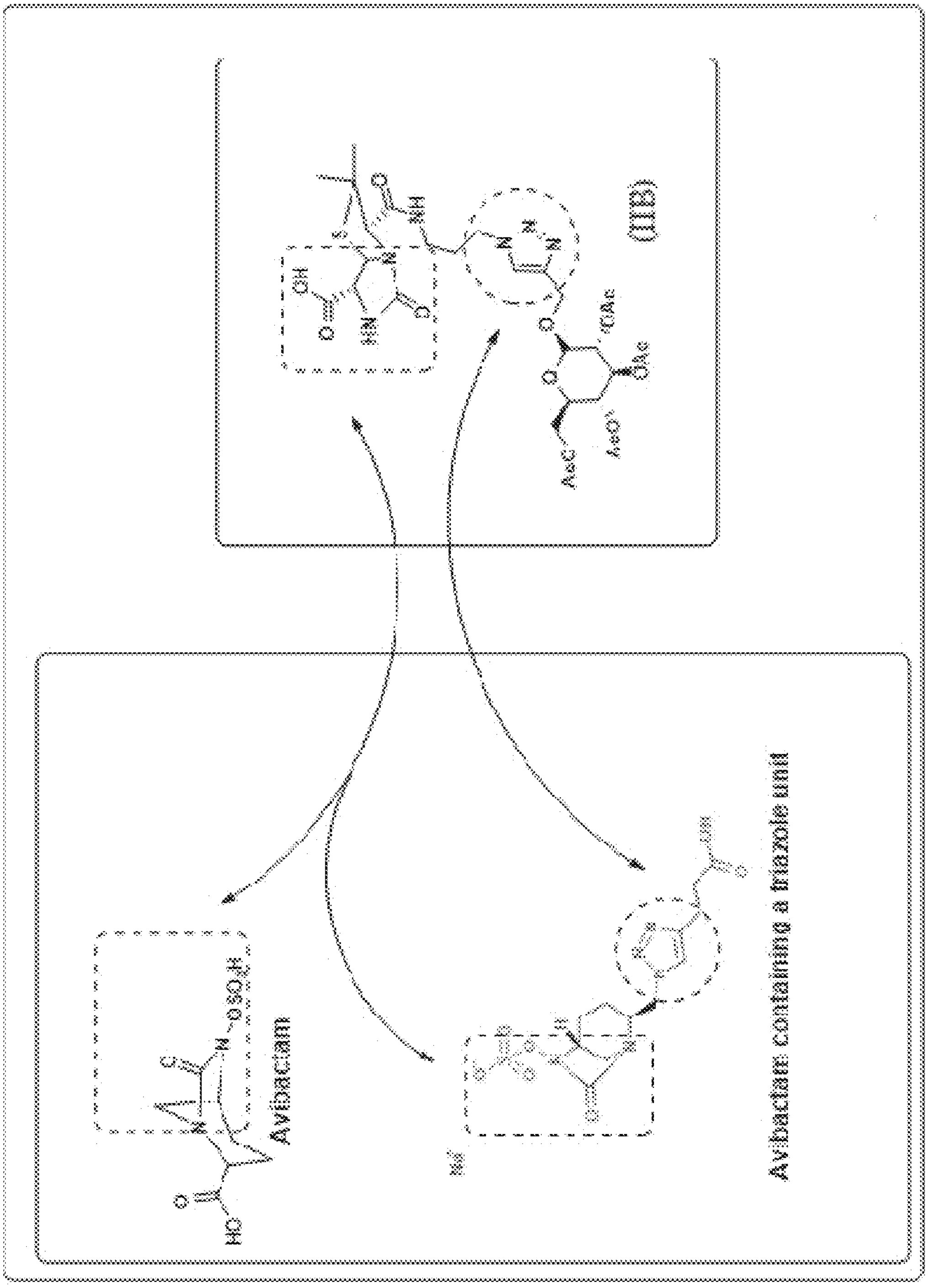
FIG. 11 shows a structural similarity between the products according to the present invention and the structure of avibactam and derivatives.

In FIG. 11, a structural similarity can be observed between the products according to the present invention and the structure of avibactam and derivatives.

It should also be pointed out that the synthesis of Avibactam and derivatives requires numerous chemical steps (more than twelve)[(26)], whereas the synthesis of the products according to the present invention requires only four steps which are, in order, N-Boc protection of 'the penicillan ring, amidation of the carboxyl group with an amine containing one or two azide groups, [3+2] cycloaddition mediated by Cu (I) and quantitative deprotection (elimination of the tert-butyl group) by means of trifluoroacetic acid ($CF_3COOH$) in accordance with the process according to the present invention.

Consequently, thanks to a particularly simple synthesis process and in the light of a completely unexpected result in terms of products obtained (opening of the beta-lactam ring with imidazolin-2-one ring rearrangement), the process according to the present invention allows new products to be obtained, that may already be interesting from a pharmacological point of view or which can be used as precursors for producing new active molecules with a broad spectrum of action both as antimicrobials, therefore useful for the fight against the bacterial resistance phenomenon, but also as possible antiviral and anticancer agents.

The following examples are representative of the present invention, without limiting its scope in any way.

EXAMPLE 1

General procedure for the preparation of derivatives of 8-hydroxypenillic acid (II) starting from secondary and tertiary amide derivatives of the 6-aminopenicillanic nucleus protected as tert-butylcarbamate (I).

0.03 mmoles of any amide derivative of the protected 6-aminopenicillanic nucleus such as tert-butylcarbamate, selected from compounds (IA), (IB) or (IC), were dissolved in 1 ml of anhydrous dichloromethane. 1.5 mmoles (50 eq.) of trifluoroacetic acid (TFA) were subsequently added to the solution at 0° C. The reaction was left under magnetic stirring for 30 minutes.

The solvent and excess TFA were removed by vacuum evaporation (rotavapor).

Figure 12:
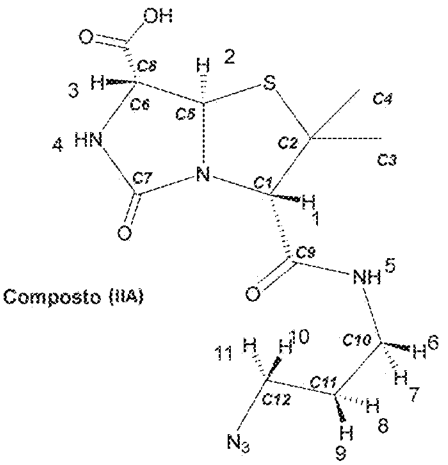
FIG. 12 shows the structure of compound (IIA) (3S,7R, 7aR)-3-((3-azidopropyl) carbamoyl)-2,2-dimethyl-5-oxo-hexahydroxyimidazo[5,1-b]thiazole-7-carboxylic acid.
Figure 13:
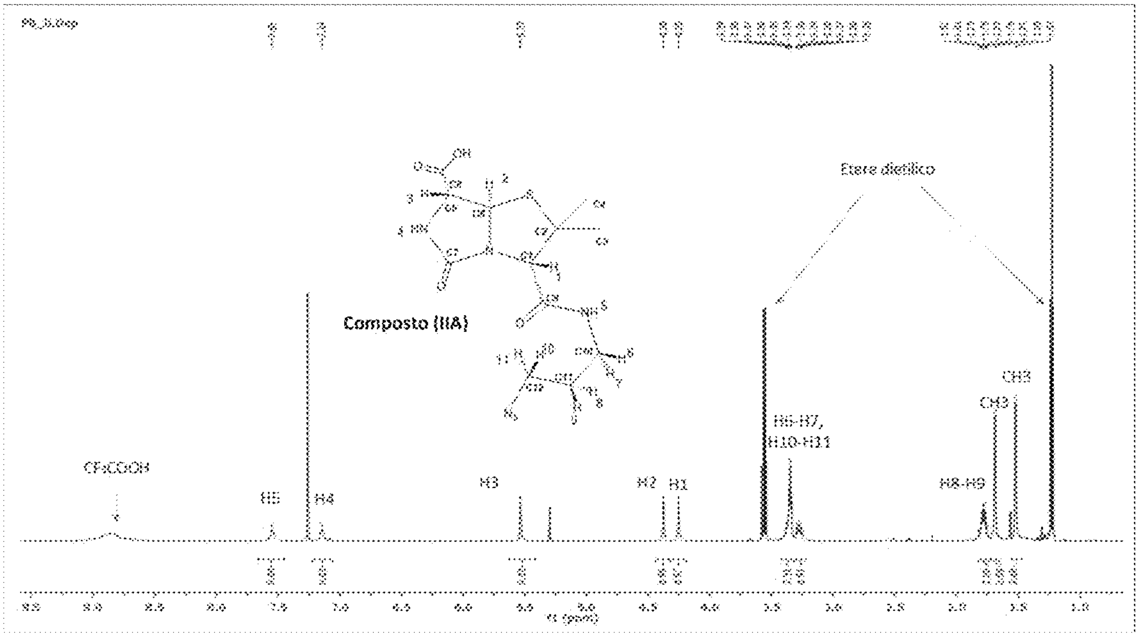
FIGS. 13-18 show the complete 1-H, 13C, COSY, HSQC and HMBC NMR analyses of the product (IIA).
Figure 14:
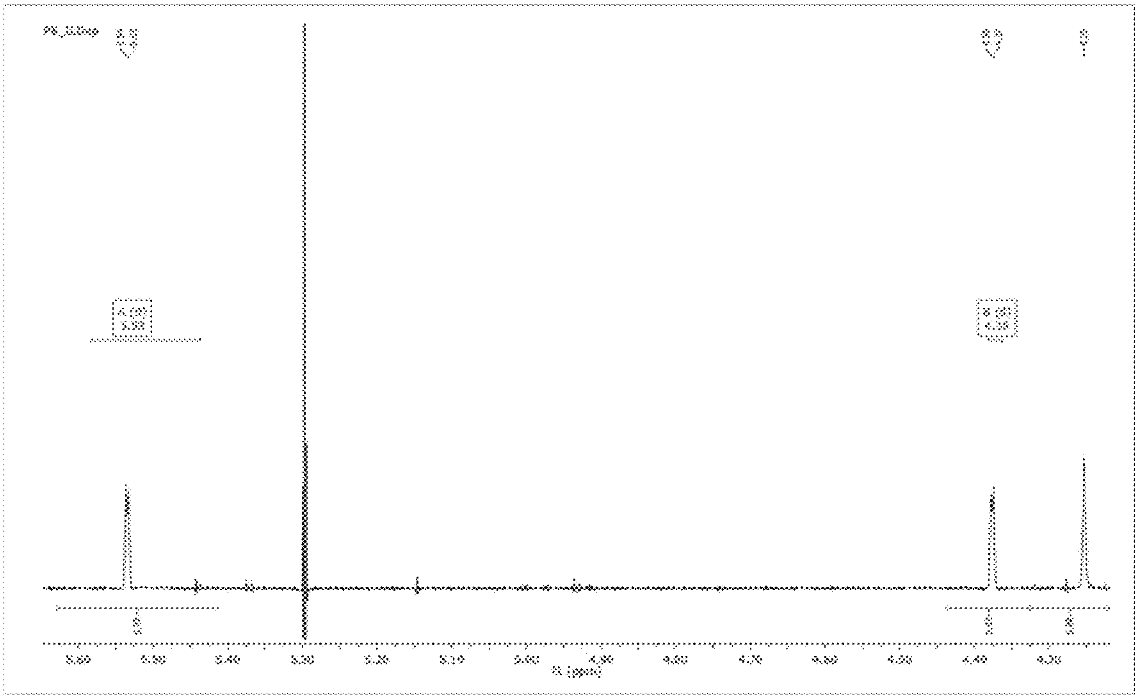
Figure 15:
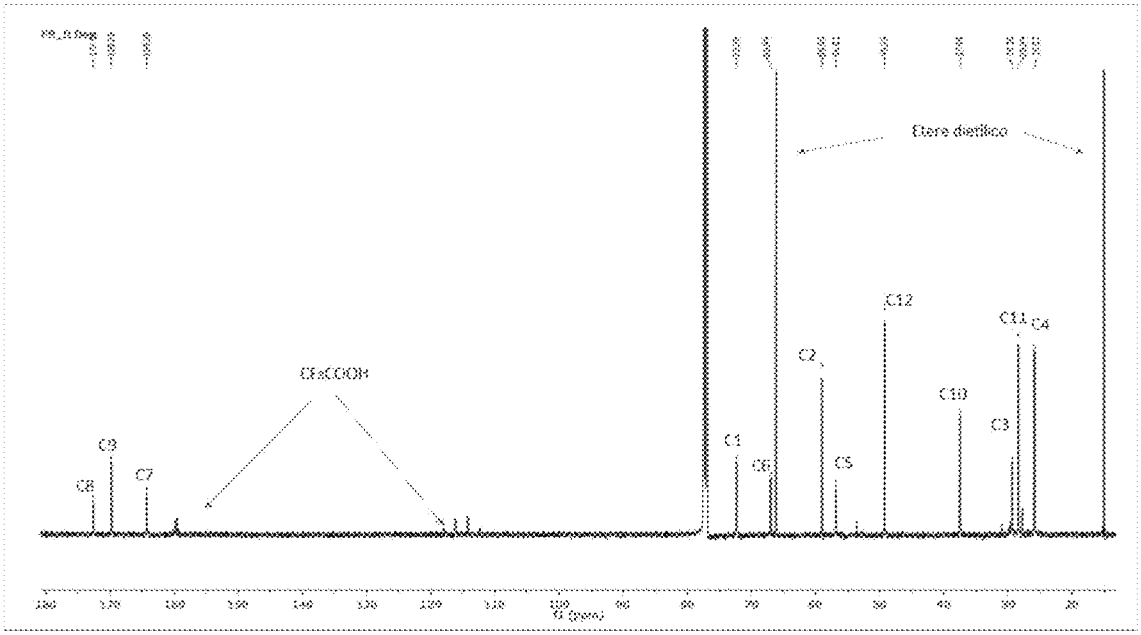
Figure 16:
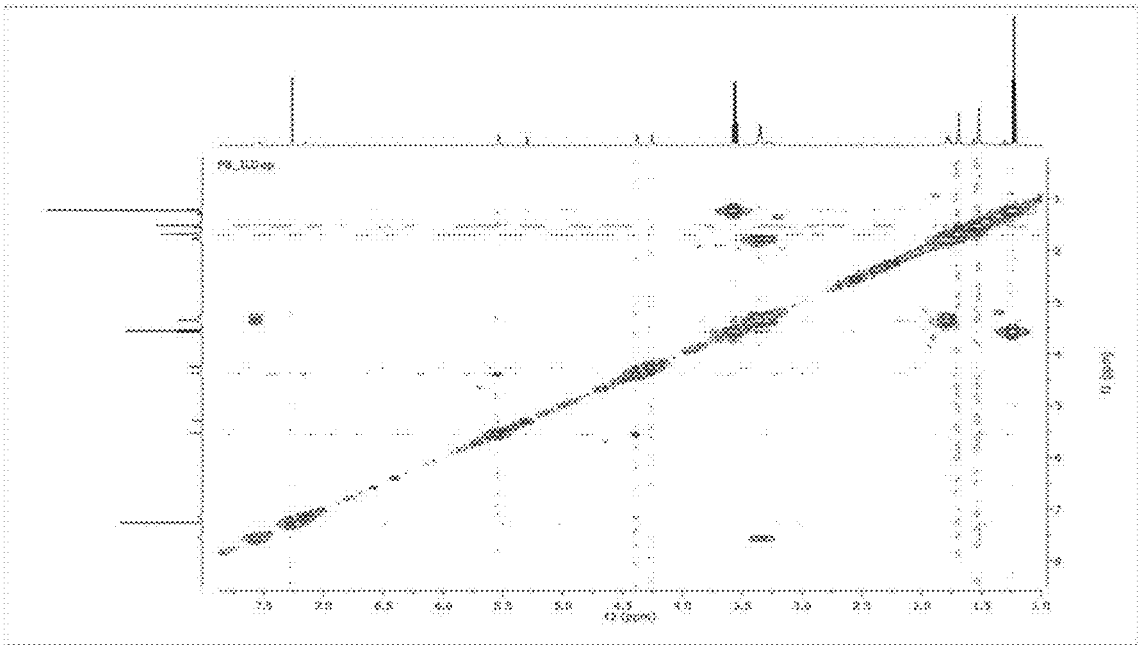
Figure 17:
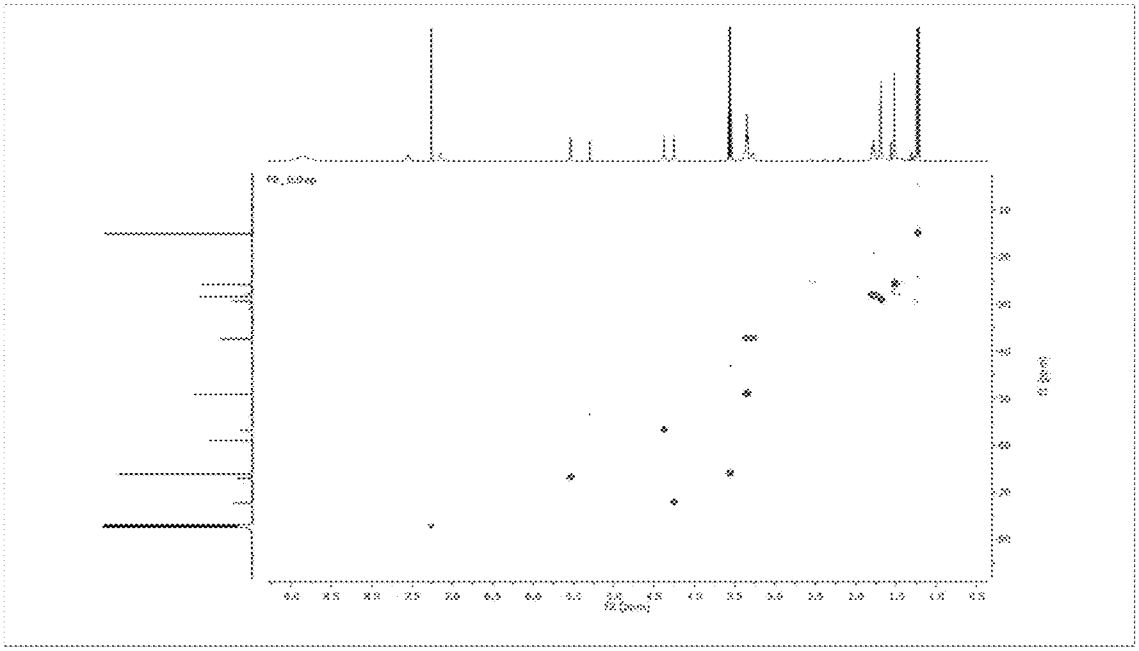
Figure 18:
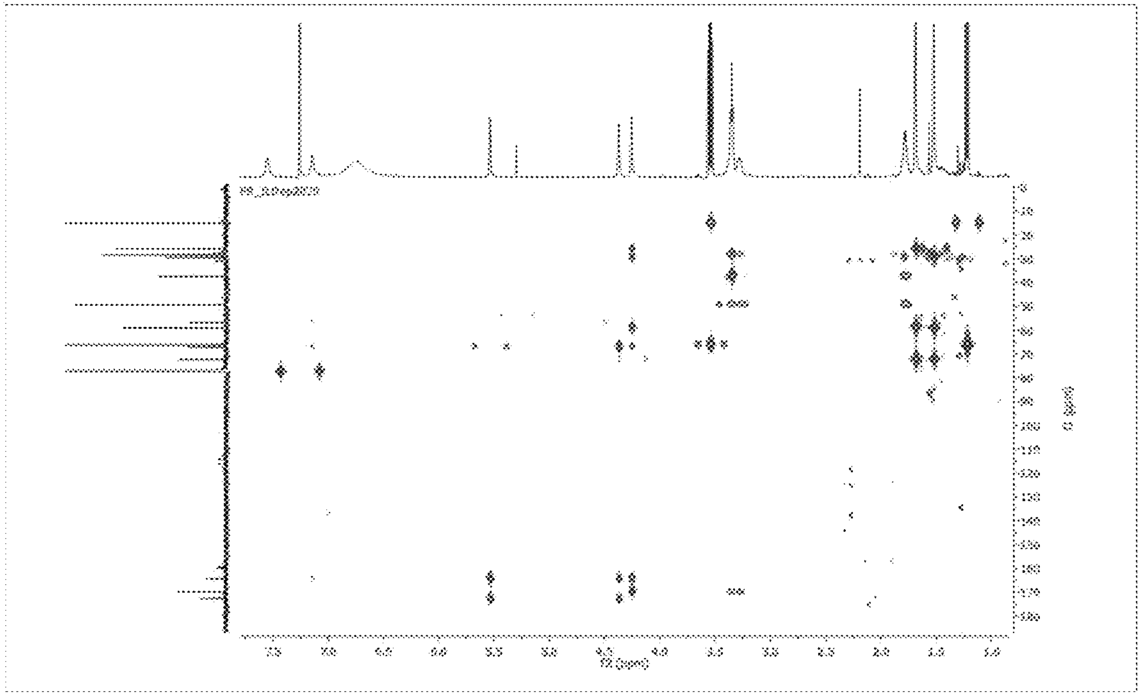

Synthesis of Compound (IIA): (3S,7R,7aR)-3-((3-azidopropyl)carbamoyl)-2,2-dimethyl-5-oxohexahydroxyimidazo[5,1-b]thiazole-7-carboxylic acid (FIG. 12)

100 μL of TFA (1.31 mmoles), 50/1 in an mmolar ratio with compound (IA), were added to a solution containing 10 mg of compound (IA) (0.026 mmoles) in anhydrous dichloromethane (1 ml) at 0° C. The reaction was kept under stirring at room temperature for 30 minutes.

After evaporation of the solvent and excess trifluoroacetic acid by means of a rotavapor, about 10 mg of a transparent chloroform-soluble oil were obtained.

The product (IIA) thus obtained, after being washed with diethyl ether in order to eliminate any traces of the starting product, was dissolved in 700 μL of $CDCl_3$ (deuterated chloroform) and subjected to complete characterization by NMR analysis ($^1H$, $^{13}C$, COSY, HCQC and HMBC) to determine its structure with accuracy.

The presence of compound (IIA) alone in the NMR, associated with the complete recovery of the starting mass and the lack of traces of the starting product (IA) in the washing solution with diethyl ether, coincide with a quantitative conversion of the starting product (IA) in the final product (IIA).

$^1H$ NMR (600 MHz, CDCl3) δ7.75 (s, 1H, H5), 7.14 (s, 1H, H4), 5.53 (d, J=1.9, H2), 4.38 (d, J=1.9, 1H, H3), 4.25 (s, 1H, H1), 3.39-3.34 (m, 3H, H10, H11, H7), 3.30-3.25 (m, 1H, H6), 1.8-1.75 (m, 2H H8-H9), 1.69 (s, 3H, CH3), 1.52 (s, 3H, CH3)

$^{13}C$ NMR (151 MHz, $CDCl_3$) δ172.59 (s, 1C, C8), 169.76 (s, C, C9), 164.28 (s, 1C, C7), 72.28 (s, 1C, C1), 66.99 (s, 1C, C5), 59.00 (s, 1C, C2), 56.81 (s, 1C, C6), 49.23 (s, 1C, C12), 37.44 (s, 1C, C10), 29.36 (s, 1C, C3), 28.39 (s, 1C, C11), 25.87 (s, 1C, C4)

In the 1H NMR spectra, the presence of diethyl ether signals at ppm 3.46 and 1.28, and those of trifluoroacetic acid at ppm 9, can be observed. The corresponding signals are obviously also found in the analysis of carbon 13.

With respect to the NMR spectrum, two important observations can be made:

- the evident elimination of the tert-butyloxy carbonyl group, $(CH_3)_3COC{=}O$, as the characteristic peak at 1.44 of the 9 Hs of the three $CH_3$ groups in the $^1H$ NMR analysis, is absent, and also in the $^{13}C$ NMR analysis, the carbonyl group at 154 ppm, the quaternary carbon at 81 ppm and the peak at 28.4 ppm typical of the three carbons of the tert-butyl group disappear. This demonstrates the deprotection reaction caused by trifluoroacetic acid;
- the rearrangement of the β-lactam ring (four ring) to 5-membered cyclic urea, to give the 8-hydroxypenillic nucleus. This rearrangement is clarified by the NMR analyses.

The $^1H$ analysis shows the presence of an excess proton compared to the $^1H$ analysis which should have resulted from the structure of the 6-aminopenicillanic nucleus if the loss of the tert-butyloxy $(CH_3)_3COC{=}O$ group had taken place without rearrangement. The 7.14 ppm signal which integrates exactly 1 as shown in the structure indicated in FIG. 12, should in fact not have existed.

In addition, the displacement of the proton signals H1, H2, H3 and H4 are not in line with the structure of 6-aminopenicillanic acid.

The H2 was assigned to the doublet at ppm 5.53 (d, J=1.9, H3) having the carbon at ppm 66.99 (s, 1C, C5) based on HSQB and HMBC analyses.

Furthermore, in the $^{13}$C NMR analysis, the presence of three peaks at ppm 172.99 (s, 1C, C8), 169.76 (s, C, C9), 164.28 (s, 1C, C7) relating to three carbonyl groups is indicated. Obviously, if the β-lactam structure had remained intact, the presence of only two carbonyl groups should have been observed, that of the 4-membered β-lactam nucleus (cyclic amide) and the carbonyl of the amide produced according to the process described in IT102018000007656.

The irrefutable evidence of the successful opening of the β-lactam ring and the subsequent closure to give a 5-membered cyclic urea resides in the NMR HMBC analysis. The carbonyl at 164.28, in fact, "sees" the H1, H2, H3 protons.

These correlations are only possible in the case of a cyclic structure such as that of 8-hydroxypenillic acid.

It has therefore been shown that, by means of the use of trifluoroacetic acid, the elimination of the tert-butyl group $(CH_3)_3COH$) is obtained with preservation of the carbonyl group (C═O) of the protective group (tert-butyloxycarbonyl $(CH_3)_3COC$═O) in the new 5 ring.

A reaction carried out starting from 20 mg of compound (IA) in 1 ml of anhydrous dichloromethane at 0° C. with a 1/100 molar ratio with trifluoroacetic acid (TFA) was effected without the subsequent washing with diethyl ether to analyze the raw reaction product.

Figure 19:
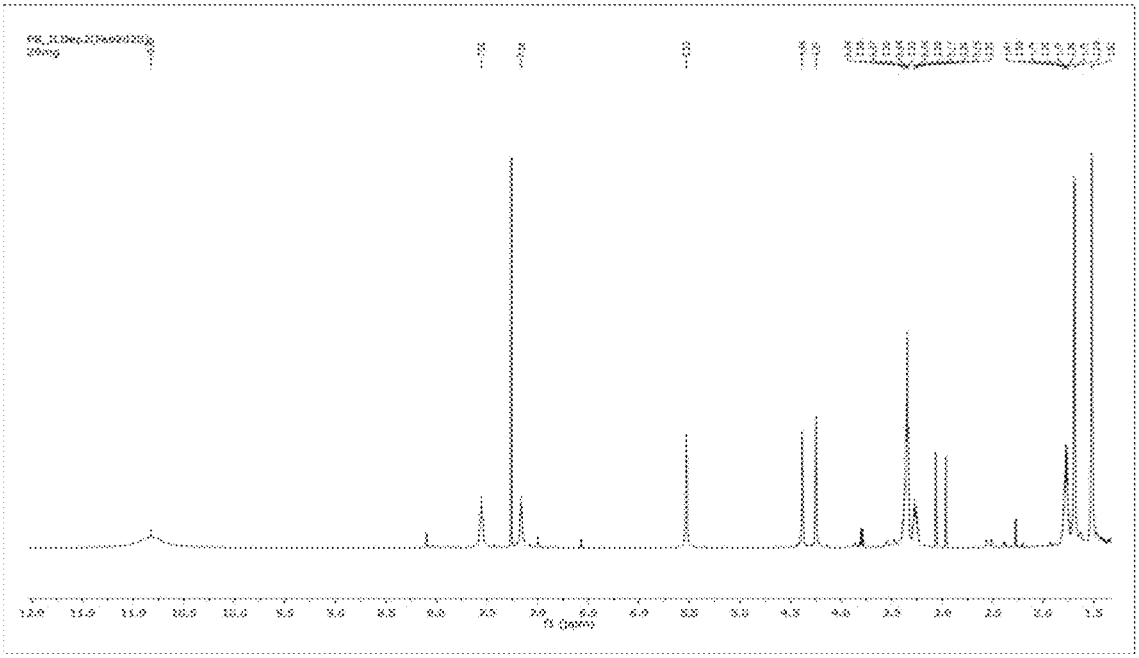
FIG. 19 shows the 1-H NMR analysis of the product (IIA) without the subsequent washing in ether.

The complete NMR analysis confirmed the quantitative conversion of compound (IA) into compound (IIA). The 1-H, 13C, COSY, HSQC and HMBC NMR analyses of the product (IIA) (FIGS. 13-18), obtained as indicated above, and the 1-H analysis of the synthesized product (IIA) without the subsequent washing in ether (FIG. 19), were recorded in support of this. Diethyl ether is therefore not present.

EXAMPLE 2

Figure 20:
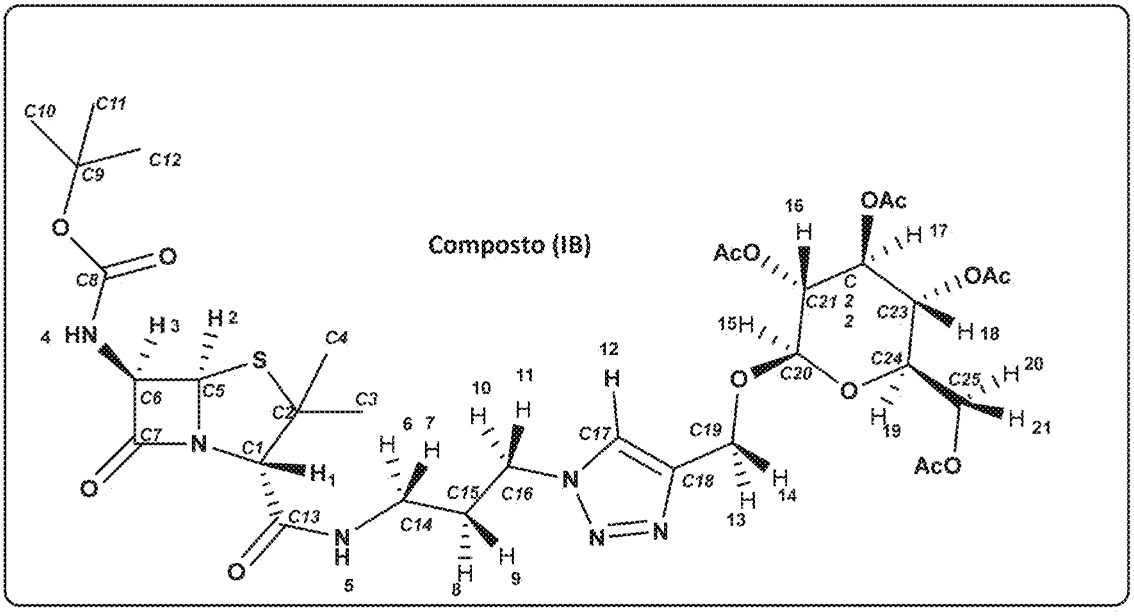
FIG. 20 shows the structure of compound (IB) (2R, 3R, 4S, 5R, 6R)-2-(acetoxymethyl)-6-((1-(3-((2S,5R, 6R)-6-((tert-butoxycarbonyl)amino)-3,3-dimethyl-7-oxo-4-thia-1-azabicyclo[3.2.0] heptane-2-carboxamido)propyl)-1H-1,2,3-triazol-4-yl)methoxy)tetrahydro-2H-pyran-3,4,5-triyl triacetate.

Synthesis of Compound (IB): (2R, 3R, 4S, 5R, 6R)-2-(acetoxymethyl)-6-((1-(3-(( 2S,5R,6R)-6-((tert-butoxycarbonyl)amino)-3,3-dimethyl-7-oxo-4-thia-1-azabicyclo [3.2.0]heptane-2-carboxamido) propyl)-1H-1,2,3-triazol-4-yl)methoxy)tetrahydro-2H-pyran-3,4,5-triyl triacetate (FIG. 20)

Compound (IB) (FIG. 20), precursor of compound (IIB) (FIG. 21), was synthesized as indicated in patent Nr. 102018000007656 by means of a cycloaddition reaction catalyzed by copper in combination with 1-O-propargyl-2,3,4,6-tetra-O-acetyl-β-D-glucose, commercially available.

Figure 22:
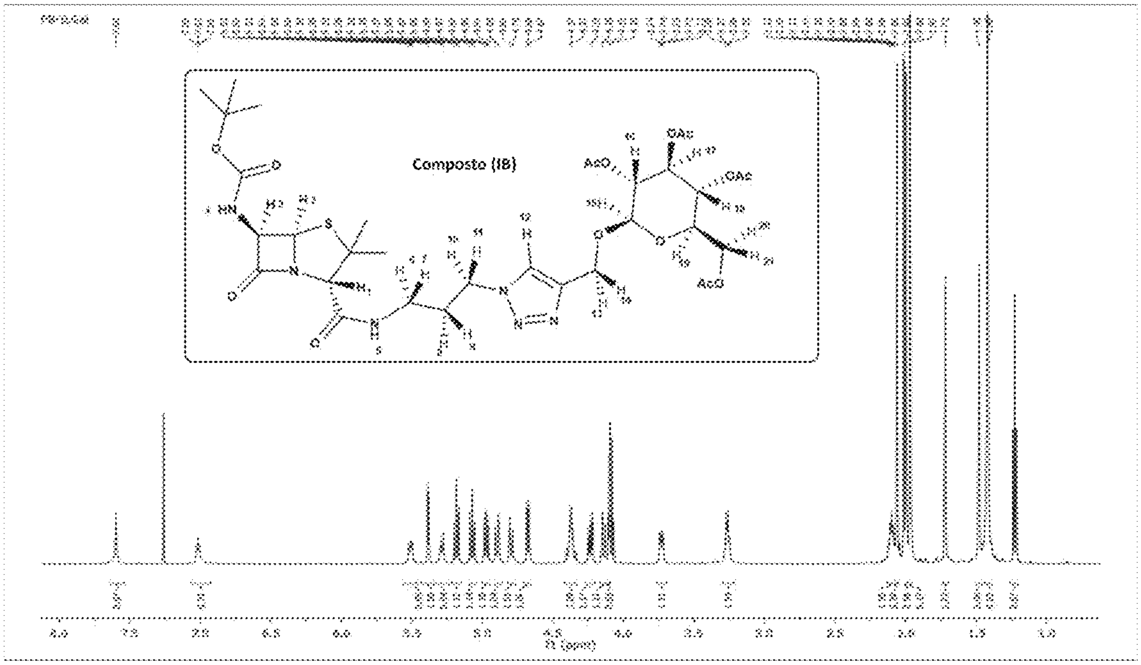
FIG. 22 shows the 1-H NMR analysis of the product (IB).
Figure 23:
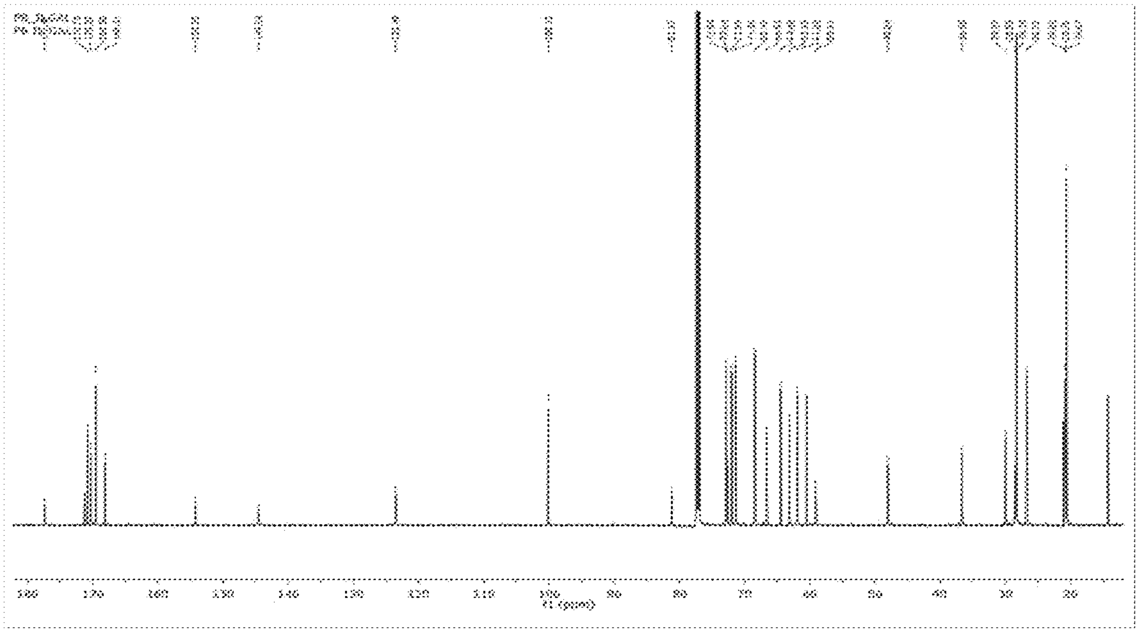
FIG. 23 shows the 13C NMR analysis of the product (IB).
Figure 24:
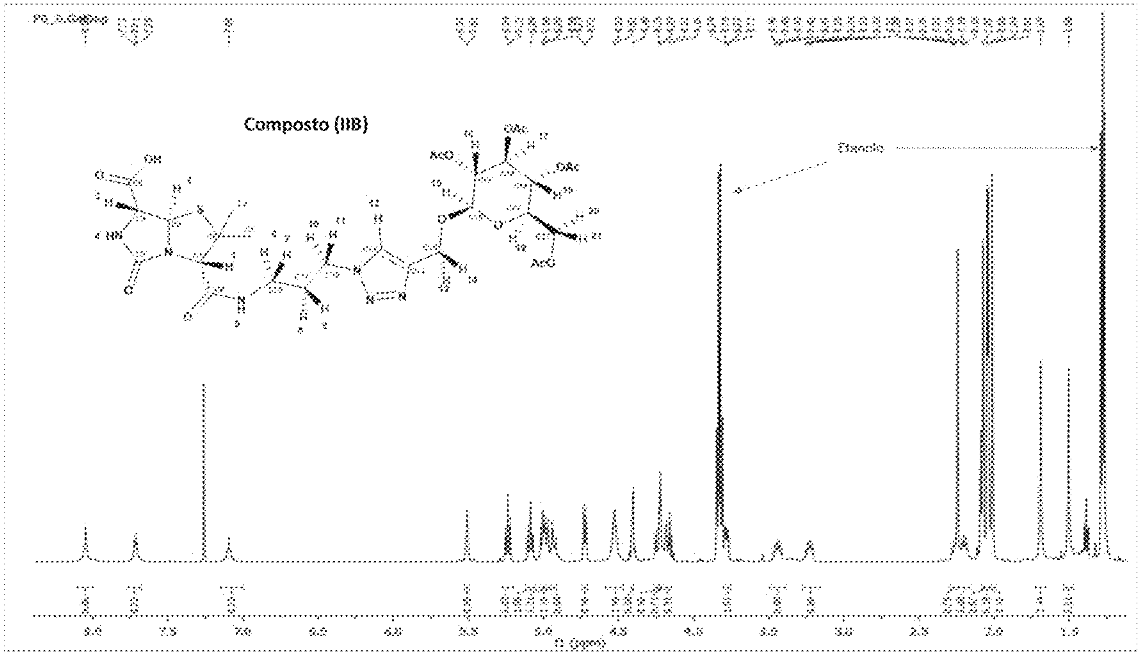
FIGS. 24-28 show the complete 1-H, 13C, COSY, HSQC and HMBC NMR analyses of the product (IIB).
Figure 25:
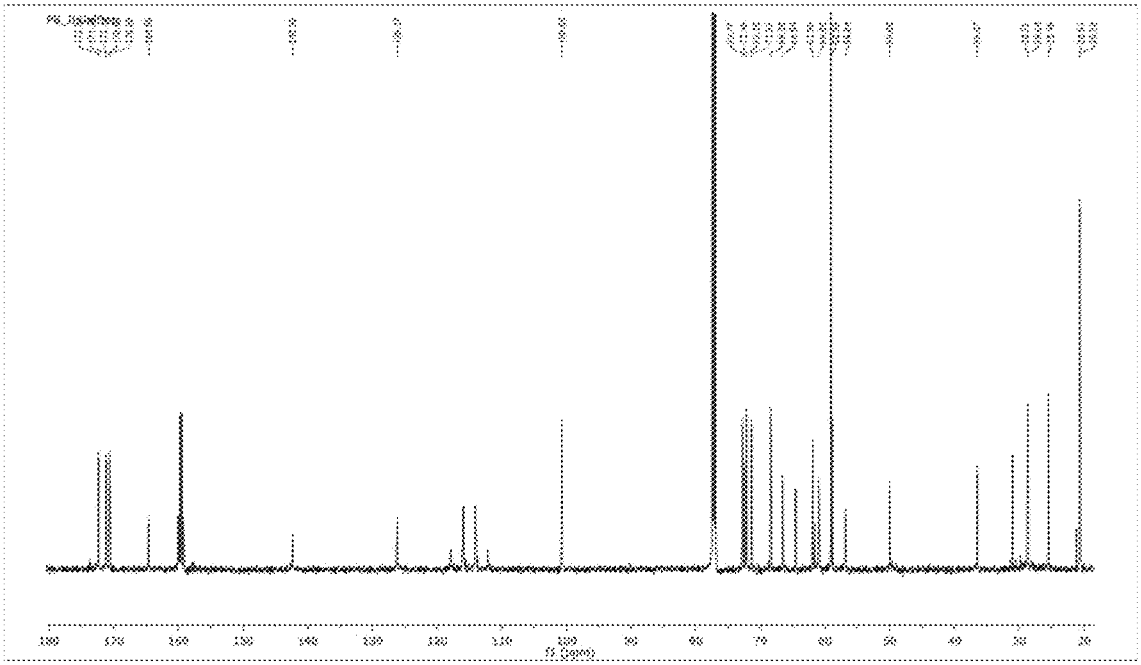
Figure 26:
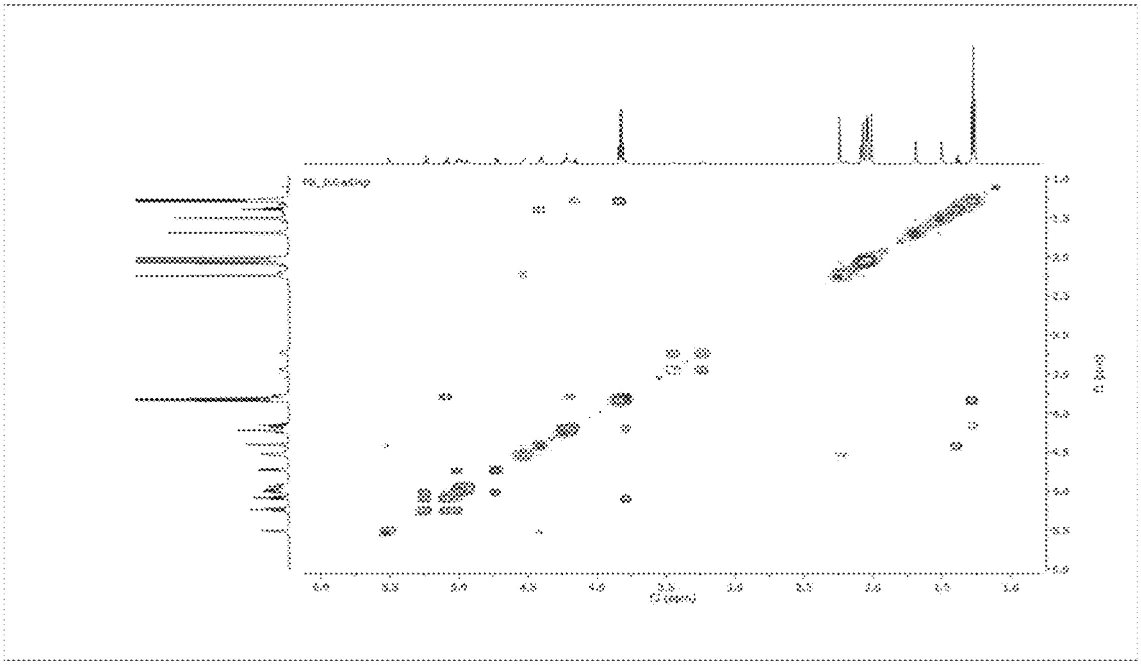
Figure 27:
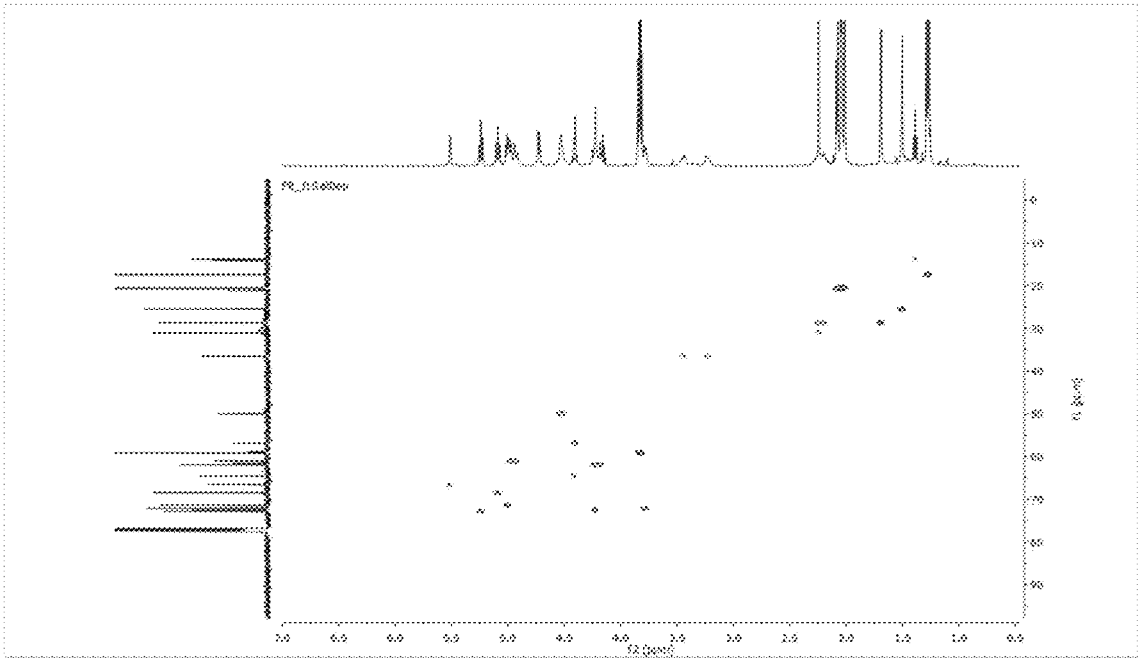
Figure 28:
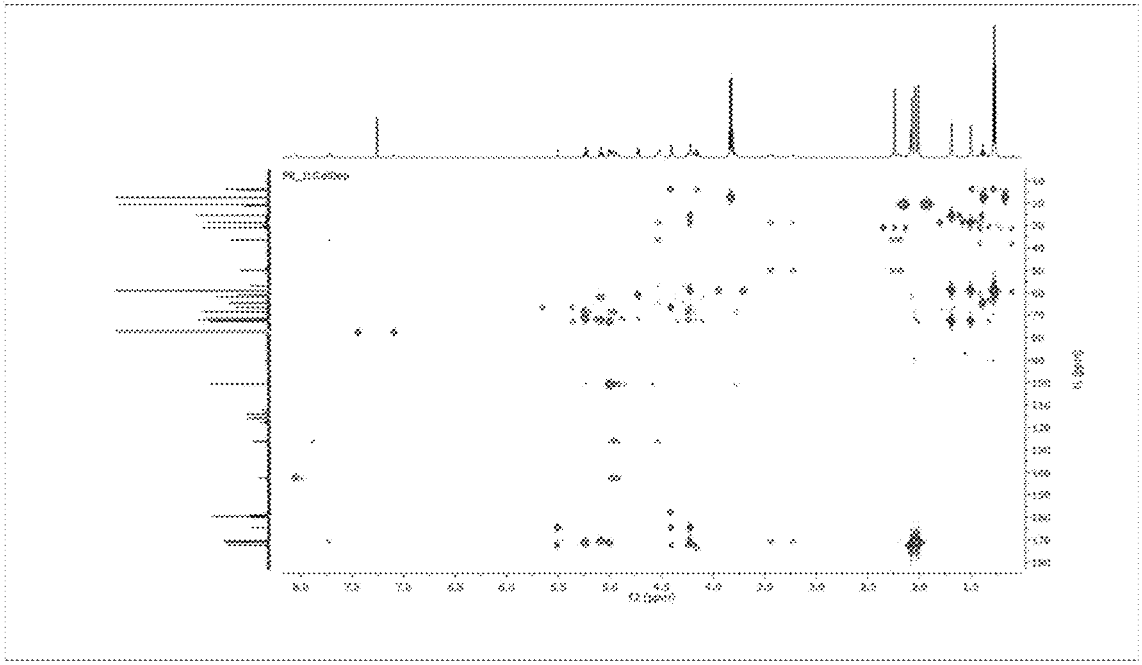

The product (IB), obtained in the form of a white solid, was characterized by complete NMR analysis (FIGS. 22 and 23). The only impurity was found to be composed of traces of ethyl acetate.

$^{1}$H NMR (600 MHz, CDCl3) δ7.60 (s, H12, 1H), 7.02 (t, J=6.0 Hz, H5 1H), 5.51 (m, H2, 1H), 5.38 (d, J=4.5 Hz, H3, 1H), 5.29 (d, J=10.3 Hz, H4, 1H), 5.18 (t, J=9.5 Hz, H17, 1H), 5.07 (t, J=9.7 Hz, H18, 1H), 4.97 (dd, J=9.4, 8.1 Hz, H16, 1H), 4.90 (d, J=12.6 Hz, H13, 1H), 4.80 (d, J=12.6 Hz, H14, 1H), 4.68 (d, J=8.0 Hz, H15, 1H), 4.42-4.33 (m, H12-H11, 2H), 4.23 (dd, J=12.3, 4.6 Hz, H21, 1H), 4.14 (dd, J=12.3, 2.0 Hz, H20, 1H), 4.10 (s, H1, 1H), 3.73 (ddd, J=10.1, 4.6, 2.4 Hz, H19, 1H), 3.26 (dd, J=12.9, 6.5 Hz, H6-H7, 2H), 2.13-2.08 (m, H8-H9, 2H), 2.06 (s, CH3COO—, 3H), 2.00 (s, CH3COO—, 3H), 1.97 (s, CH3COO—, 6H), 1.72 (s, CH3—, 3H), 1.48 (s, CH3—, 3H), 1.42 (s, Boc, 9H), $^{13}$C NMR (151 MHz, CDCl3) δ177.36 (s, C7, 1C), 170.78 (s, OAc, 1C), 170.27 (s, 1C, OAc), 169.50 (s, 2C, OAc), 168.11 (s, C13, 1C), 154.25 (s, 1C, C8), 144.54 (s, 1C, C18), 123.49 (s, C17, 1C), 100.13 (s, 1C, C20), 81.17 (s, 1C, C9), 72.84 (s, C22, 1C) 72.64 (s, C1, 1C), 71.99 (s, C24, 1C), 71.36 (s, C23, 1C), 68.42 (s, C22, 1C), 66.61 (s, C5, 1C), C64.48 (s, C2, 1C), 63.13 (s, C19, 1C), 61.89 (s, C25, 1C), 59.11 (s, C6, 1C), 48.04 (s, C16, 1C), 36.65 (s, C14, 1C), 29.97 (s, C15, 1C), 28.53, (s, C3, 1C), 28.28 (s, C10-C11-C12, 3C), 26.73 (s, C4, 1C), 20.85 (s, OAc, 1C), 20.76 (s, OAc, 1C), 20.67 (s, OAc, 2C).

Figure 21:
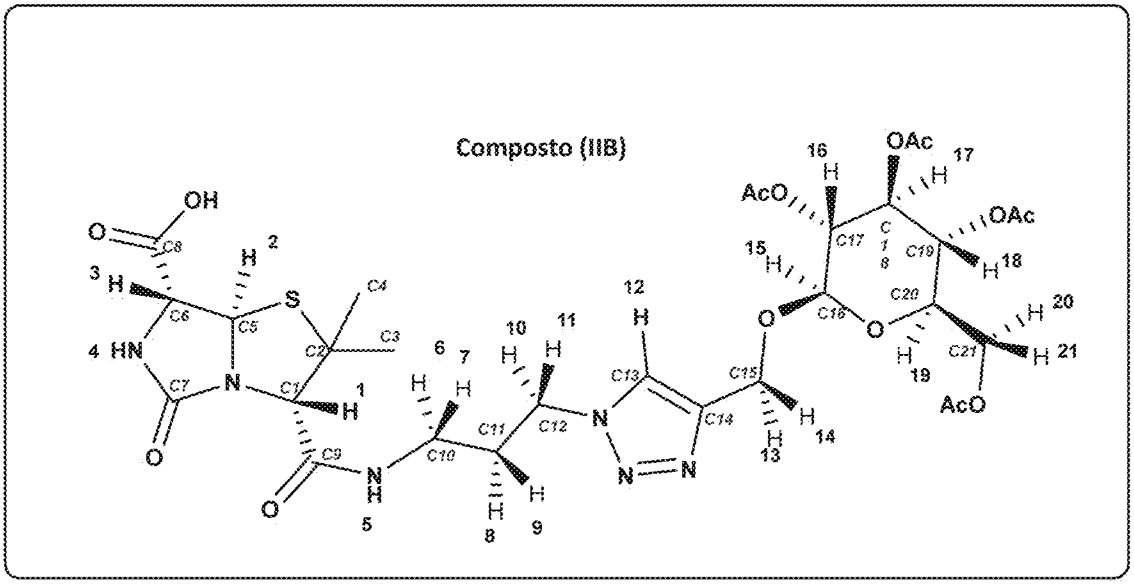
FIG. 21 shows the structure of compound (IIB) (3S, 7R, 7aR)-2,2-dimethyl-5-oxo-3-((3-(4-((((2R, 3R, 4S, 5R, 6R)-3,4,5-triacetoxy-6-(acetoxymethyl) tetrahydro-2H-pyran-2-yl)oxy) methyl)-1H-1,2,3-triazol-1-yl)propyl)carbamoyl) hexahydroimidazo[5,1-b]thiazole-7-carboxylic acid.

Synthesis of compound (IIB): (3S, 7R, 7aR)-2,2-dimethyl-5-oxo-3-((3-(4-((((2R, 3R, 4S, 5R, 6R)-3,4,5-triacetoxy-6-(acetoxymethyl) tetrahydro-2H-pyran-2-yl) oxy) methyl)-1H-1,2,3-triazol-1-yl) propyl)carbamoyl)hexahydroimidazo[5,1-b]thiazole-7-carboxylic acid (FIG. 21)

Following the procedure previously indicated in Example 1, the compound (IB) was subjected to the deprotection reaction with trifluoroacetic acid, obtaining compound (IIB) (FIG. 21) which was then characterized by complete NMR analysis (FIGS. 24-28).

$^{1}$H NMR (600 MHz, CDCl3 Rapid) d 8.05 (s, 1H, H12), 7.71 (t, J=5.6 Hz, H5, 1H), 7.09 (s, H4, 1H), 5.51 (d, J=1.9 Hz, H2, 1H), 5.24 (t, J=9.5 Hz, H17, 1H), 5.08 (t, J=10.3 Hz, H18, 1H), 5.00 (dd, J=9.7, 7.9 Hz, H16, 1H), 4.98 (d, J=14.2 Hz, H13, 1H), 4.93 (d, J=14.2 Hz, H14, 1H), 4.72 (d, J=7.9 Hz, H15 1H), 4.53 (td, J=6.7, 2.5 Hz, H10-H11, 2H), 4.40 (s, H3, 1H), 4.24 (dd, J=12.5, 2.3 Hz,H20, 1H), 4.22 (s, H1, 1H), 4.17 (dd, J=12.7, 4.6 Hz, H21, 1H), 3.78 (ddd, J=10.1, 4.4, 2.4 Hz, H19, 1H), 3.47-3.41 (m, H6, 1H), 3.25-3.20 m, H7, 1H), 2.28-2.18 (m, H8-H9, 2H), 2.07 (s, OAc, 3H), 2.05 (s, OAc, 3H) 2.04 (s, OAc, 3H), 2.01 (s, OAc, 3H), 1.69 (s, CH3, 3H), 1.50 (s, CH3, 3H).

$^{13}$C NMR (151 MHz, CDCl3) d 172.34 (s, 1C, C8), 171.20 (s, 1C, OAc), 171.14 ((s, 1C, OAc), 170.62 (s, 2C, OAc), 170.60 (s, 1C, C9), 164.60 (s, 1C, C7), 142.32 (s, 1C, C14), 126.17 (s, 1C, C13), 100.69 (s, 1C, C16), 72.77 (s, 1C, C18), 72.46 (s, 1C, C1), 72.15 (s, 1C, C20), 71.37 (s, 1C, C17), 68.39 (s, 1C, C19), 66.54 (s, 1C, C5), 61.90 (s, 1C, C21), 60.95 (s, 1C, C15), 58.93 (s, 1C, C2), 56.84 (s, 1C, C6), 50.00 (s, 1C, C12), 36.47 (s, C10, 1C), 28.71 (s, C3, 1C), 28.64 (s, C11, 1C), 25.46 (s, C4, 1C), 20.65 (s, OAc, 1C), 20.61 (S, OAc, 1C), 20.58 (s, OAc, 2C)

Also in this case, the reaction took place with a quantitative yield. The impurities present, whose peaks were omitted from both the $^{1}$H-NMR analysis and the $^{13}$C-NMR analysis, are ethanol, acetone, diethyl ether and TFA.

There are no signs of degradation of the compound (IIB). Consequently, as in the previous example 1, the reaction took place rapidly and with a total rearrangement of the 5-membered β-lactam nucleus containing cyclic urea.

The loss of the tert-butyl group at 1.44 (deprotection completed) is evident, as is also the presence of a carbonyl group at 164.60 ppm typical of the cyclic urea of 8-hydroxypenillic acid, analogously to compound (IIA).

The same considerations made for compound (IIA) also apply to compound (IIB).

EXAMPLE 3

Figure 29:
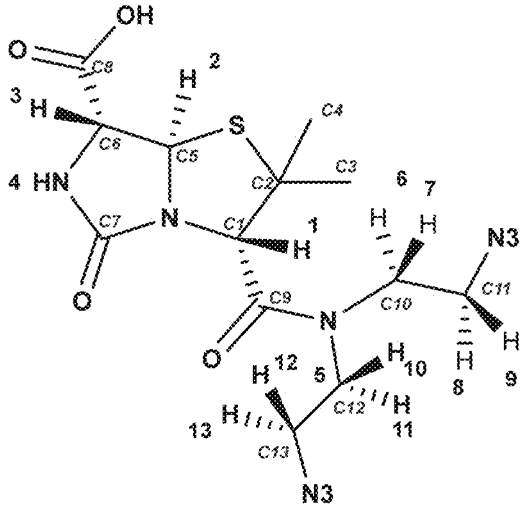
FIG. 29 shows the structure of compound (IIC) (3S, 7R, 7aR)-3-((bis (2-azidoethyl)carbamoyl)-2,2-dimethyl-5-oxo-hexahydroimidazo[5,1-b]thiazole-7-carboxylic acid.

Synthesis of compound (IIC): (3S, 7R, 7aR)-3-((bis(2-azidoethyl)carbamoyl)-2,2-dimethyl-5-oxohexahydroimidazo[5,1-b]thiazole-7-carboxylic acid (FIG. 29)

Compound (IIC) (FIG. 29) was synthesized following the procedure of the previous Example 1, starting from compound (IC), described in European patent application EP3626721A1.

Also in this case, deprotection took place with the removal of the tert-butyl group and a complete conversion of the β-lactam ring with the formation of 5-membered cyclic urea by incorporation of the carbonyl (tert-butyloxycarbonyl) in the new cycle that was formed.

Figure 30:
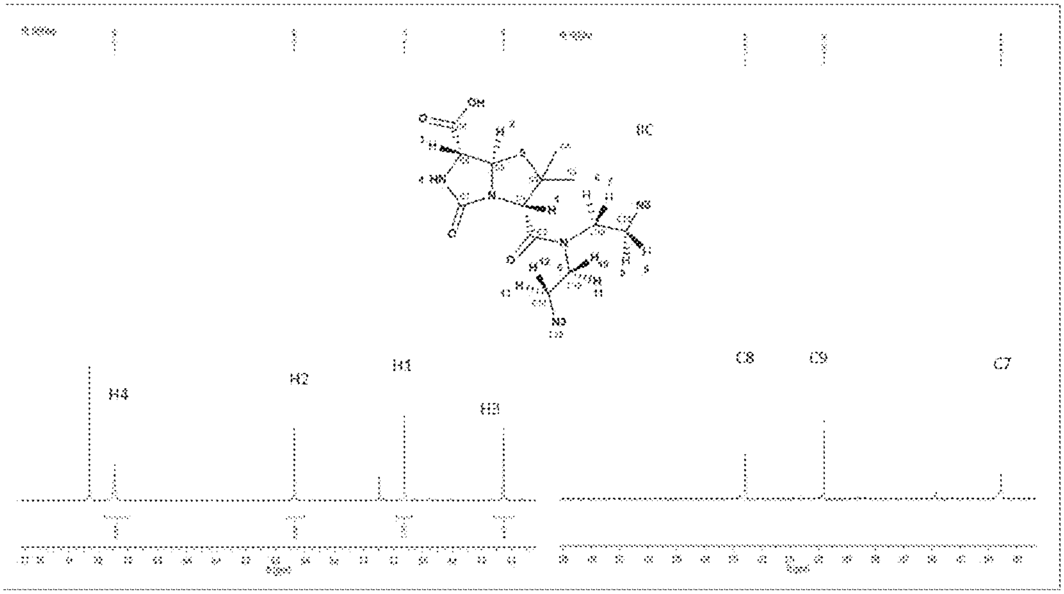
FIGS. 30-32 show the complete 1-H, 13C and COSY NMR analyses of the product (IIC).
Figure 31:
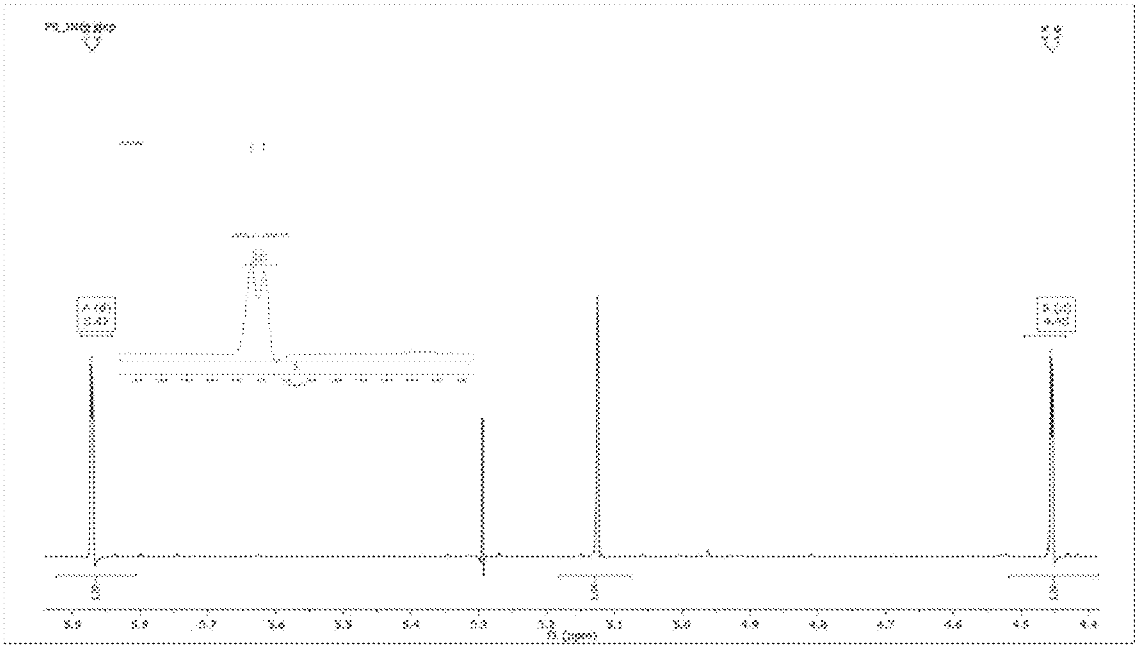
Figure 32:
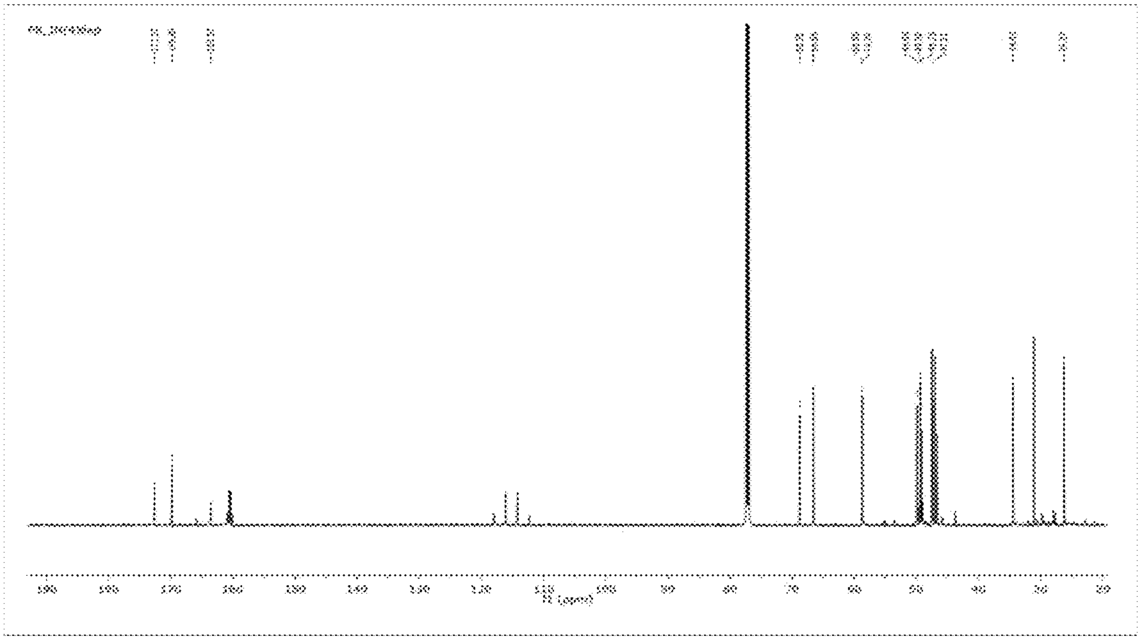

The molecule and the structure of compound (IIC) were characterized by NMR analysis (1H, 13C, COSY) (FIGS. 30-32).

In FIGS. 30 and 31, the peaks relating to the protons H1, H2, H3, H4 and the three characteristic carbonyls C7, C8 and C9 can be observed, demonstrating the formation of cyclic urea (FIGS. 30-31).

$^{1}$H NMR (600 MHz, $CDCl_3$) δ8.36, (br, COOH, 1H), 7.09 (s, 1H), 5.87 (d, J=1.5 Hz, H2 1H), 5.13 (s, H1, 1H), 4.45 (d, J=1.6 Hz, H3 1H), 3.89 (dt, J=14.0, 4.6 Hz, H6, 1H), 3.67-3.59 (m, H8-H9-H10-H11-H12-H13, 6H), 3.25-3.20 (m, H7, 1H), 1.57 (s, $CH_3$, 3H), 1.55 (s, $CH_3$, 3H).

$^{13}$C NMR (151 MHz, CDCl3) δ172.57 (C8), 169.80 (C9), 163.57 (C7), 68.75 (C5), 66.56 (C1), 58.80 (C2), 58.70 (C6), 49.88 (C12), 49.38 (C13), 49.23 (C11), 47.31 (C10), 34.43 (C3), 26.27 (C4).

Synthesis of Compounds (IID) and (IIE)

Compound (ID) and compound (IE), were obtained using HATU (1-[Bis(dimethylamino)methylene]-1H-1,2,3-triazol[4,5-b]pyridinium 3-oxide hexafluorophosphate) as the conjugation agent in the presence of Triethylamine (TEA) or Diisopropylethylamine (DIPEA).

To 1 millimole of starting substrate, compound (ID), in 20 mL of anhydrous DCM (dichloromethane), 1 millimole of HATU was added at room temperature and then two equivalents of TEA and one equivalent of propargylamine were added.

To 1 millimole of starting substrate, compound (IE), in 20 mL of anhydrous DCM (dichloromethane), 1 millimole of HATU was added at room temperature and then 2 equivalents of DIPEA and 1 equivalent of dipropargylamine were added.

After leaving under stirring for a time of about 4 hours, the reaction mixture was treated with water saturated with NaCl and extracted with DCM. After anhydrification with sodium sulfate and evaporation with rotavapor, the crude product was purified by flash chromatography using a hexane/ethylacetate 6/4 mixture as eluent.

The product was obtained as a white foam with a yield of 50%.

The (ID) and (IE) substrates were then treated with TFA as disclosed in Example 1, yielding the (IID) and (IIE) products in quantitative yield as pale straw yellow oils. The loss of the protective group and the appearance of a carbonyl were also detected for the (ID) and (IE) compounds, reflecting the formation of the new 5-ring as confirmed by the two-dimensional NMR analysis (HSQC and HMBC).

Compound (ID)

Figure 34:
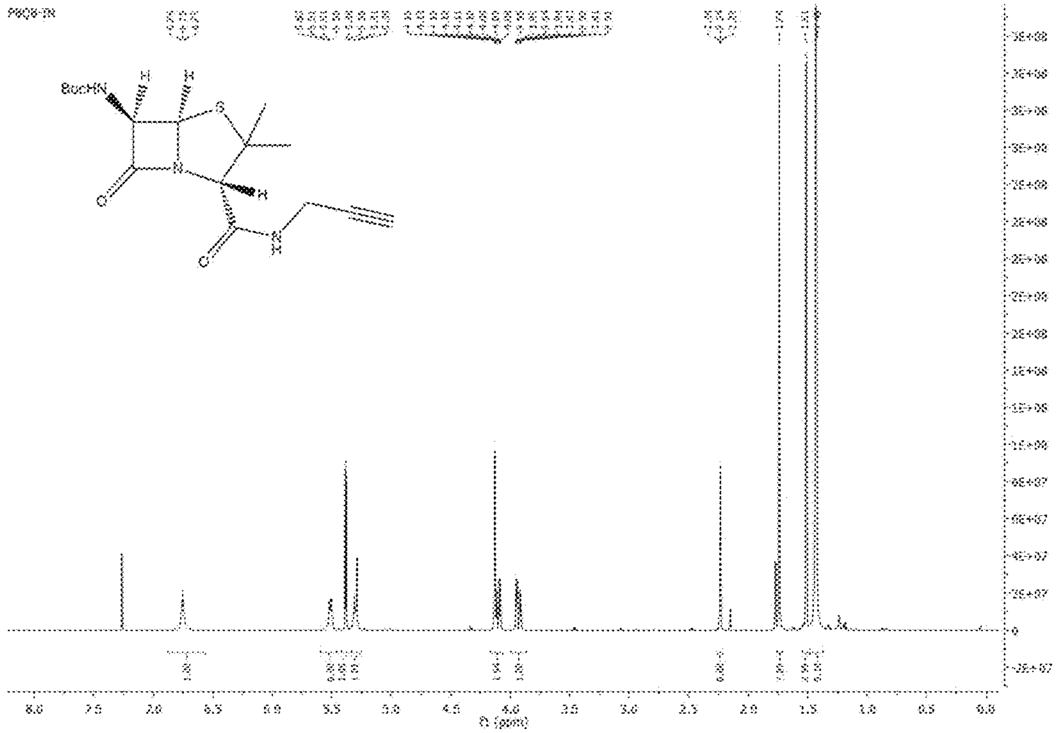
FIG. 34 shows the complete 1-H NMR analysis of the product (ID): tert-butyl ((2S,5R,6R)-3,3-dimethyl-7-oxo-2-(prop-2-yn-1-yl) carbamoyl)-4-thia-1-azabicyclo[3.2.0]heptan-6-yl)carbamate.

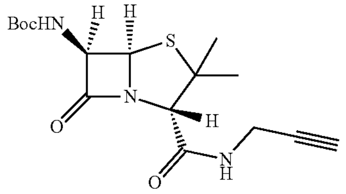

tert-butyl ((2S,5R,6R)-3,3-dimethyl-7-oxo-2-(prop-2-yn-1-yl)carbamoyl)-4-thia-1-azabicyclo[3.2.0]heptan-6-yl)carbamate $^{1}$H NMR (600 MHz, $CDCl_3$) δ6.79-6.70 (m, 1H), 5.51 (dd, J=9.8, 4.3 Hz, 1H), 5.38 (d, J=4.6 Hz, 1H), 5.30 (d, J=9.9 Hz, 1H), 4.13 (s, 1H), 4.10 (ddd, J=17.6, 5.9, 2.5 Hz, 1H), 3.93 (ddd, J=17.6, 5.0, 2.6 Hz, 1H), 2.24 (t, J=2.6 Hz, 2H), 1.74 (s, 3H), 1.51 (s, 3H), 1.43 (s, 9H) (FIG. 34)

Compound (IE)

tert-butyl ((2S,5R,6R)-2-(di(prop-2-yn-1-yl)carbamoyl)-3,3-dimethyl-7-oxo-4-thia-1-azabicyclo[3.2.0]heptan-6-yl)carbamate

IE

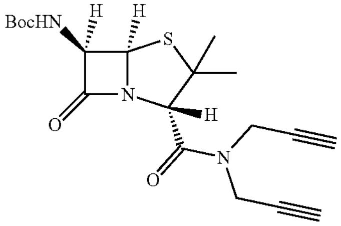

$^{1}$H NMR (600 MHz, $CDCl_3$) δ5.69 (d, J=4.2 Hz, 1H), 5.44 (dd, J=9.9, 4.2 Hz, 1H), 5.34 (d, J=10.1 Hz, 1H), 4.88 (s, 1H), 4.37-4.31 (m, 3H), 4.22 (dd, J=18.6, 2.5 Hz, 1H), 2.42 (t, J=2.5 Hz, 1H), 2.25 (t, J=2.5 Hz, 1H), 1.66 (s, 3H), 1.53 (s, 3H), 1.45 (s, 9H).

Compound (IID): (3S,7R,7aR)-2,2-dimethyl-5-oxo-3-((prop-2-yn-1-yl)carbamoyl) hexahydroimidazo[5,1-b]thiazole-7-carboxylic acid

IID

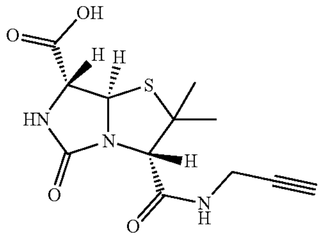

Figure 35:
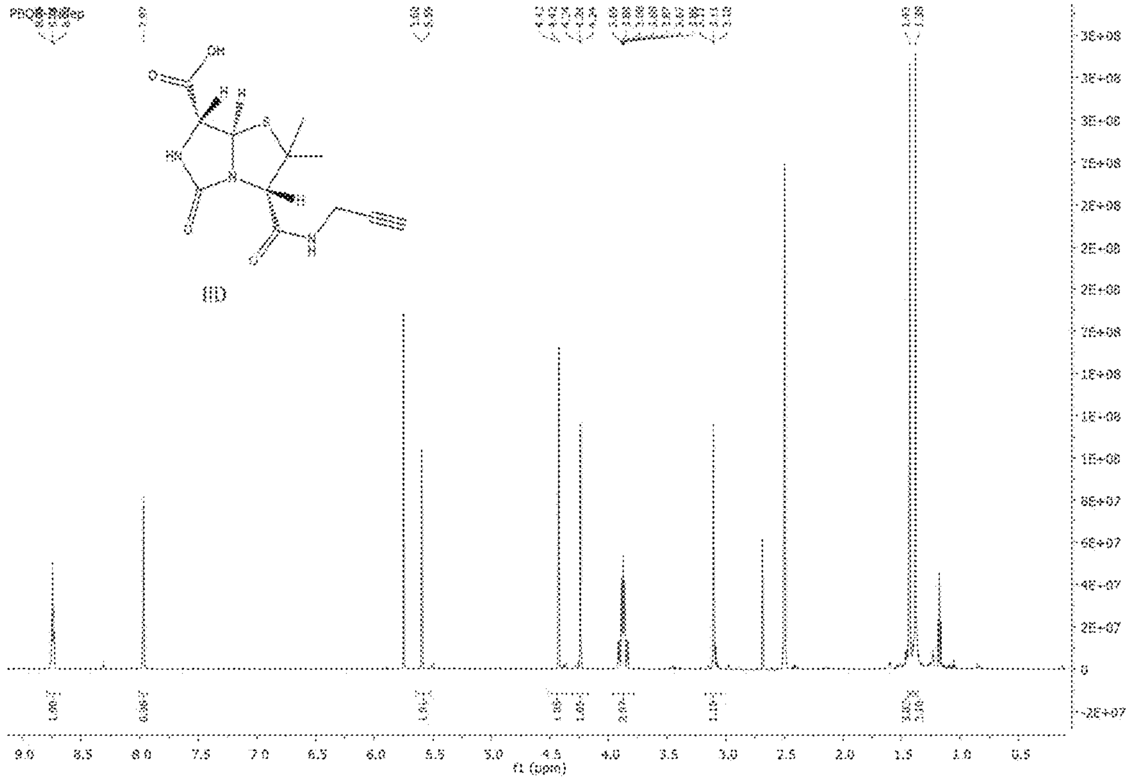
FIG. 35 shows the complete 1-H NMR analysis of the product (IID): (3S,7R,7aR)-2,2-dimethyl-5-oxo-3-((prop-2-yn-1-yl) carbamoyl) hexahydroimidazo [5,1-b]thiazole-7-carboxylic acid.

$^{1}$H NMR (600 MHz, DMSO-d6) δ13.38, (br, 1H), 8.74 (t, J=5.5 Hz, 1H), 7.97 (s, 1H), 5.60 (d, J=1.4 Hz, 1H), 4.42 (d, J=0.5 Hz, 1H), 4.24 (t, J=1.3 Hz, 1H), 3.92-3.81 (m, 2H), 3.11 (t, J=2.5 Hz, 1H), 1.43 (s, 3H), 1.38 (s, 3H) (FIG. 35)

Figure 36:
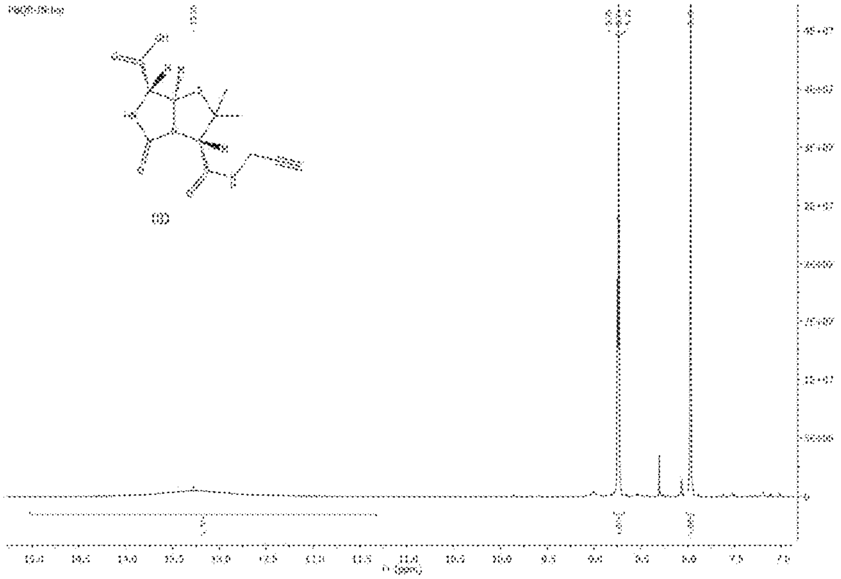
FIG. 36 shows the complete 13-C NMR analysis of the product (IID).

$^{13}C$ NMR (151 MHz, $CDCl_3$) δ172, 168.14, 161.62, 80.63, 73.07, 70.55, 68.81, 58.13, 56.95, 32.98, 27.60, 26.05 (FIG. 36)

Compound (IIE): (3S,7R,7aR)-3-(di(prop-2-yn-1-yl) carbamoyl)-2,2-dimethyl-5-oxohexahydroimidazo[5, 1-b]thiazole-7-carboxylic acid

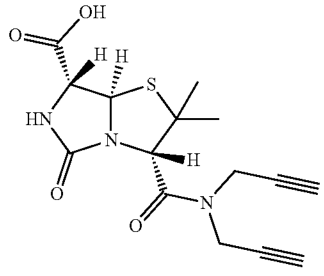

Figure 37:
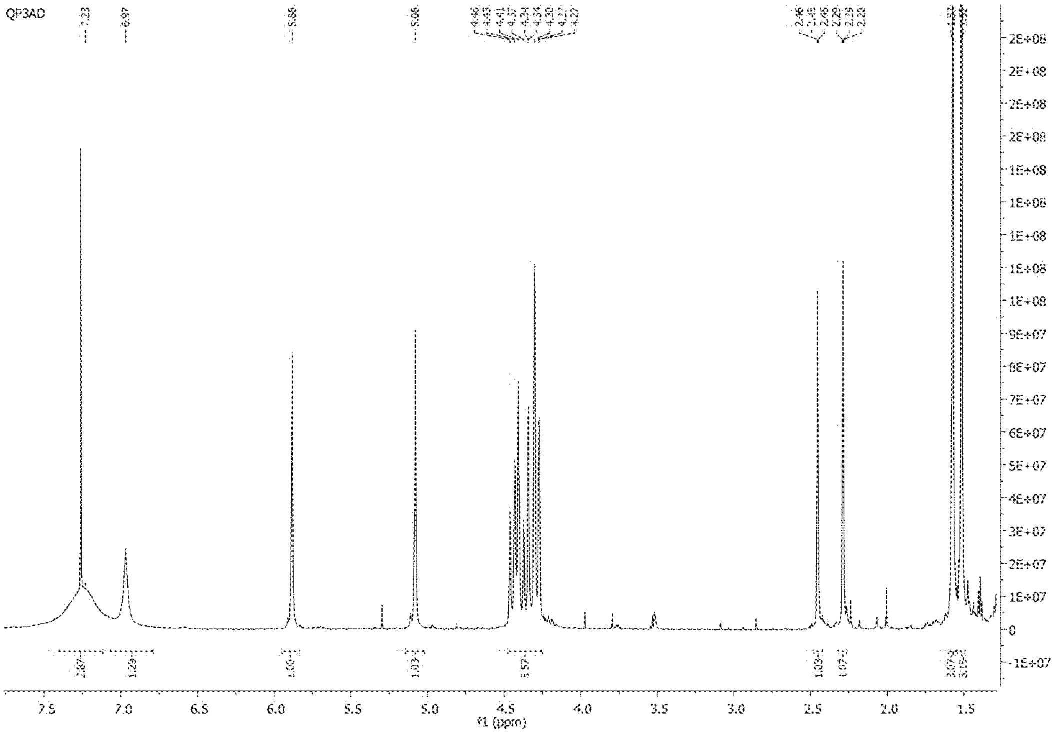
FIG. 37 shows the complete 1-H NMR analysis of the product (IIE): (3S,7R,7aR)-3-(di(prop-2-yn-1-yl) carbamoyl)-2,2-dimethyl-5-oxohexahydroimidazo[5,1-b]thiazole-7-carboxylic acid.

$^1H$ NMR (600 MHz, $CDCl_3$) δ7.23 (br, COOH), 6.97 (s, 1H), 5.88 (s, 1H), 5.08 (s, 1H), 4.47-4.25 (m, 5H), 2.45 (t, J=2.3 Hz, 1H), 2.29 (t, J=2.5 Hz, 1H), 1.57 (s, 3H), 1.52 (s, 3H) (FIG. 37)

Figure 38:
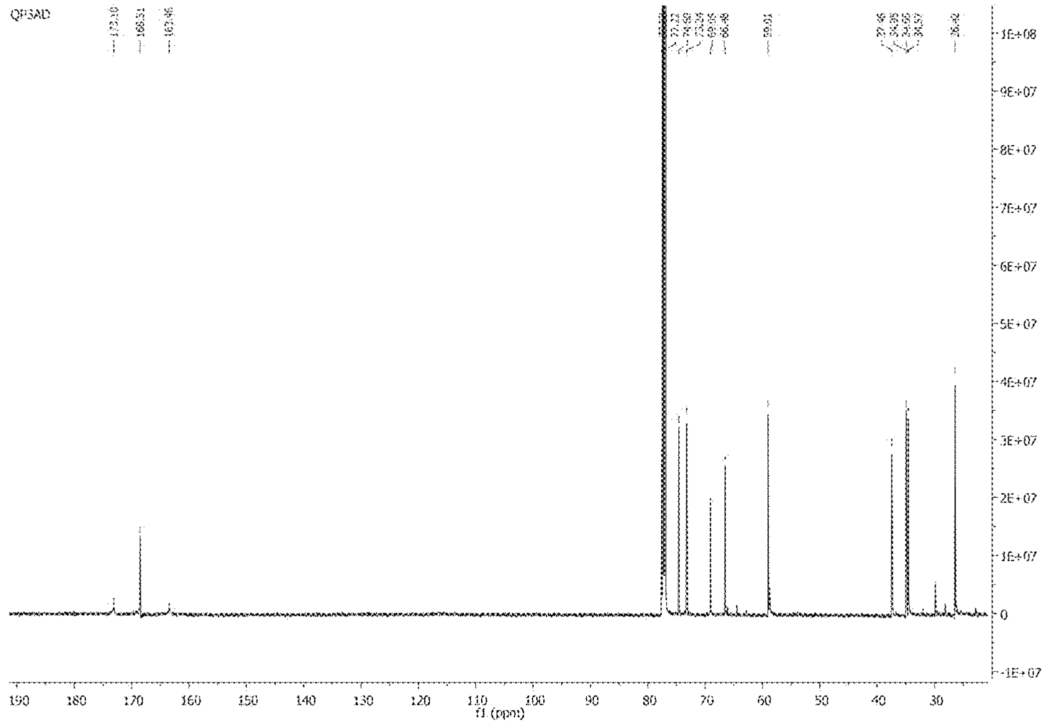
FIG. 38 shows the complete 13-C NMR analysis of the product (IIE).

$^{13}C$ NMR (151 MHz, $CDCl_3$) δ173.30, 168.51, 163.46, 77.53, 77.22, 74.80, 73.24, 69.05, 66.48, 59.00, 58.75, 37.46, 34.95, 34.57, 26.42 (FIG. 38).

EXAMPLE 4

Compound IIB was tested and compared to the Penγ molecule below represented and disclosed in the patent application WO2017/153892.

Penγ

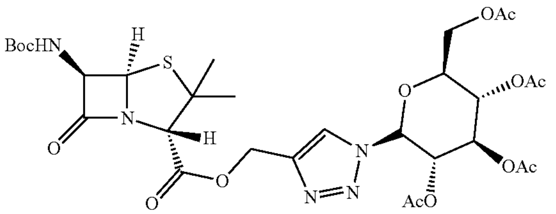

IIB

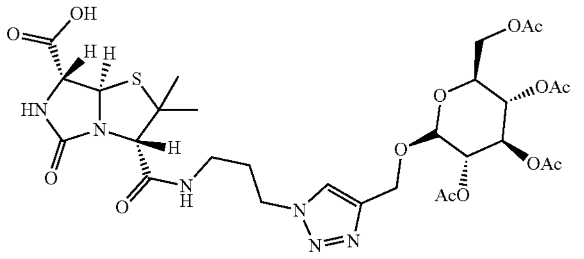

The two compounds, by means of a standard assay, were tested on mammalian (hamster) cancer cells to evaluate possible anticancer activity.

Compound (IIB) was used at concentrations of 25 μM and 50 μM, while Penγ compound was tested at concentrations up to 400 μM.

Mammalian cancer cells were then incubated for 24 hours.

Precisely, CHO-S cells were cultured in 2 mL of DMEM (Dulbecco's Modified Eagle Medium) (10% FBS, 6% Glutamax) in a 24-well plate at a density of 200×10$^3$ cells/per well and subsequently incubated at 37° C. in a controlled atmosphere (5% $CO_2$) under shaking. The following day, cells were counted by means of the Countess II instrument (Thermofisher Scientific) (an automated cell counter). They were then treated with Purymycin (positive control), Peny, (IIB) compounds, and in the absence of any product (negative control), at the concentrations shown in FIG. 37.

Cell counts were performed after 24 hours to determine the number of viable cells.

Figure 39:
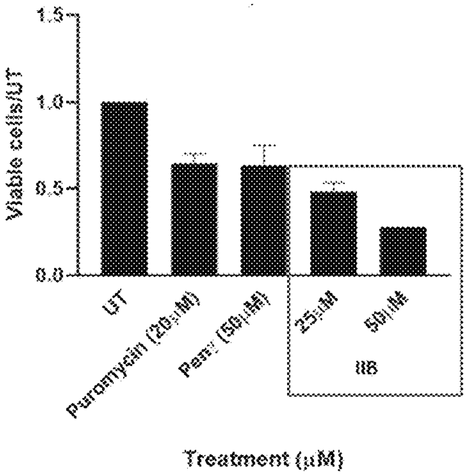
FIG. 39 is a graph showing the number of viable cells in presence of the Purymycin (positive control), Peny, IIB compounds and in the absence of any product (negative control).

The graph shown in FIG. 39 shows the number of viable cells in presence of the Purymycin (positive control), Peny, IIB compounds and in the absence of any product (negative control).

The graph shows that at a concentration of 50 μM, the compound (IIB) leads to a reduction of almost 50% of viable cells and this data shows an anticancer effect that is not associated with the Penγ compound.

REFERENCES (1) C. Lee Ventola "*The Antibiotic Resistance Crisis Part* 1: *Causes and Threats*" P T. 2015 April; 40(4):277-283

(2) W. A. Adedeji "*THE TREASURE CALLED ANTIBIOTICS*" Ann Ib Postgrad Med. 2016 December; 14(2):56-57

(3) Peter M Hawkey "*The origins and molecular basis of antibiotic resistance*" BMJ. 1998 Sep. 5; 317(7159):657-660. doi:10.1136/bmj.317.7159.657

(4) Julian Davies, Dorothy Davies "*Origins and Evolution of Antibiotic Resistance*" MICROBIOLOGY AND MOLECULAR BIOLOGY REVIEWS, September 2010, p. 417-433

(5) Waldovogel F A. "*New Resistance in Staphylococcus aureus*". N Engl J Med. 1999; 340:556-7. [PubMed]

(6) Bernardo Ribeiro da Cunha et al.; "*Antibiotic Discovery: Where Have We Come from, Where Do We Go*?" Antibiotics 2019, 8, 45; doi:10.3390/antibiotics8020045

(7) "*PRIORITIZATION OF PATHOGENS TO GUIDE DISCOVERY, RESEARCH AND DEVELOPMENT OF NEW ANTIBIOTICS FOR DRUG-RESISTANT BACTERIAL INFECTIONS, INCLUDING TUBERCULOSIS*" WHO reference number: WHO/EMP/IAU/2017.12

(8) Marco Maria D'Andrea et al "*The Urgent Need for Novel Antimicrobial Agents and Strategies to Fight Antibiotic Resistance*" Antibiotics (Basel). 2019 December; 8(4): 254

(9) Ursula Theuretzbacher et al.; «Reviving old antibiotics» J Antimicrob Chemother 2015; 70:2177-2181

(10) Kamaleddin H. M. E. Tehrania and Nathaniel I. Martin «*β-lactam/β-lactamase inhibitor combinations: an update*»: Med. Chem. Commun., 2018, 9, 1439

(11) Yu'ning Song et al.; "Old Friends in New Guise": Exploiting Privileged Structures for Scaffold Re-Evolution/Refining" Combinatorial Chemistry & High Throughput Screening, 2014, Vol. 17, No. 6, 1-18

(12) Nicole Jackson, Lloyd Czaplewski and Laura J. V. Piddock "*Discovery and development of new antibacterial drugs: learn from experience?*" J Antimicrob Chemother 2018; 73:1452-1459

(13) Pavlina Jelinkova et al.; "*Nanoparticle-drug conjugates treating bacterial infections*" Journal of Controlled Release 307 (2019) 166-185

(14) Sharada Prasanna Swain* and Sandeep Mohanty "*Imidazolidinones and Imidazolidine*-2,4-*diones as Antiviral Agents*" Chem Med Chem 2019, 14, 291-302

(15) David A. Johnson and Glenn A. Hardcastle Jr. "*REACTION OF 6-AMINOPENICILLANIC ACID WITH CARBON DIOXIDE*" J. Am. Chem. Soc. 1961, 83, 16, 3534-3535

(16) P. Dryjansk et al, "*8-Hydroxypenillic Acid from 6-Aminopenicillanic Acid:? A New Reaction Catalyzed by a Class C β-Lactamase*" [Journal of the American Chemical Society, 1996, vol. 118, #35, p. 8207-8212

(17) Chun-Jing Liu, Dinah Dutta e Lester Mitscher. "*Synthesis of new penicillin derivatives as drug-like molecules for biological screening*" Chinese Chemical Letters Volume 26, Issue 1, January 2015, Pages 113-117

(18) Marchand-Brynaert; Mougenot; Combret; Belotti; Guillot; Ghosez., "*Design, synthesis and evaluation of D, D-peptidase and beta-lactamase inhibitors: azapeptides, oxapeptides and related heterocycles*" 1995, Farmaco; vol. 50; n. 6; p. 455-469

(19) George V. De Lucca "*Synthesis and evaluation of imidazolidinones as nonpeptide HIV-protease inhibitors*" Bioorganic & Medicinal Chemistry Letters Volume 7, Issue 5, 4 Mar. 1997, Pages 495-500

(20) V. R. Pothineni et al.; "*Azlocillin can be the potential drug candidate against drug-tolerant Borrelia burgdorferi sensu stricto JLB*31" Scientific Reports volume 10, Article number: 3798 (2020)

(21) Yousry A. Ammar "*New Imidazolidineiminothione, Imidazolidin-2-one and Imidazoquinoxaline Derivatives: Synthesis and Evaluation of Antibacterial and Antifungal Activities*" Current Organic Synthesis, 2016, 13, 466-475

(22) Dmitry Pavlov "*Facile Synthesis of 3-(Azol-1-yl)-1-adamantanecarboxylic Acids—New Bifunctional Angle-Shaped Building Blocks for Coordination Polymers*" Molecules 2019, 24, 2717; doi:10.3390/molecules24152717

(23) Caitlyn M Rotondo and Gerard D Wright "*Inhibitors of metallo-b-lactamases*" Current Opinion in Microbiology 2017, 39:96-105

(24) George J. Kontoghiorghes "*Advances on Chelation and Chelator Metal Complexes in Medicine.*" Int J Mol Sci. 2020 April; 21(7):2499

(25) «*Diazabicyclooctane Functionalization for Inhibition of β-Lactamases from Enterobacteria*» J. Med. Chem. 2020, 63, 10, 5257-5273

(26) Ken Coleman "*Diazabicyclooctanes (DBOs): a potent new class of non-β-lactam β-lactamase inhibitors*" Current Opinion in Microbiology 2011, 14:550-555

(27) Poh, Jian-Siang et al. "*Rapid Asymmetric Synthesis of Disubstituted Allenes by Coupling of Flow-Generated Diazo Compounds and Propargylated Amines*"; Angewandte Chemie-International Edition, 2017, vol. 56, #7, p. 1864-1868

The invention claimed is:

1. A process for synthesis of derivatives of 8-hydroxypenillic acid starting from amide derivatives of a protected N-Boc 6 amino-penicillanic nucleus, wherein a compound having formula (I):

(I)

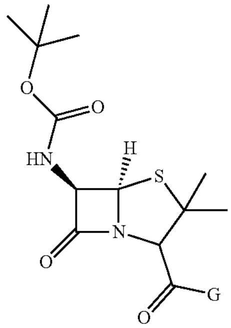

with G equal to a $NR_1R_2$ group wherein $R_1$ and $R_2$ are selected from hydrogen and a linear alkyl chain having from 2 to 5 carbon atoms with an azide group, a propargyl group or a triazole group functionalized with a saccharide, wherein $R_1$ and $R_2$ are not simultaneously equal to hydrogen, or wherein the compound is (ID)

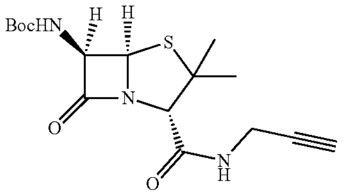

or (IE)

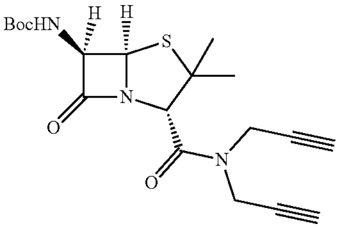

, is subjected to a deprotection reaction or wherein the compound is (ID)

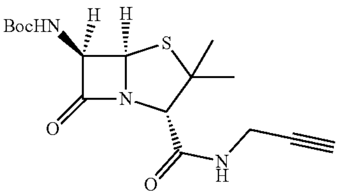

or (IE)

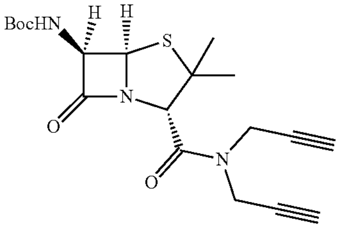

, carried out in the presence of an excess of trifluroacetic acid (TFA) in a polar solvent, at a temperature ranging from 0° C. to room temperature, for a period of time ranging from 5 minutes to 2 hours, obtaining a compound having formula (II):

(II)

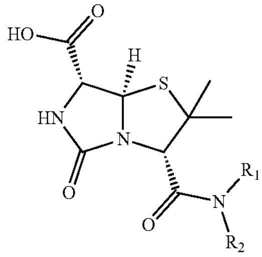

wherein $R_1$ and $R_2$ have the meanings previously indicated.

2. The process according to claim 1, wherein the compounds having formula (I) are secondary or tertiary amide derivatives of the 6-APA nucleus, protected on the amino group as tert-butyl carbamate selected from compounds (IA), (IB), (IC), (ID) and (IE) indicated hereunder:

(IA)

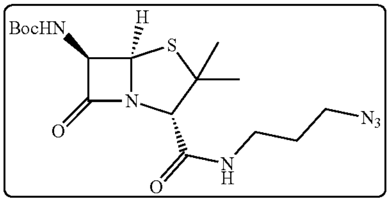

(IB)

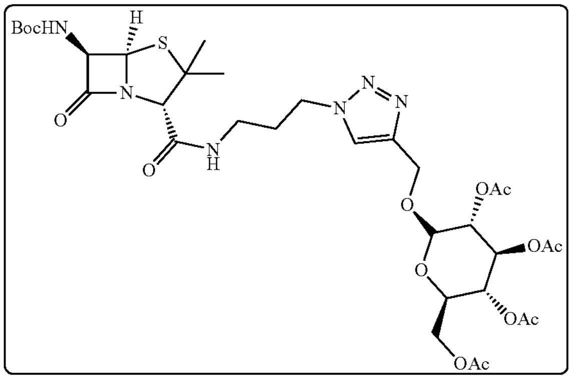

(IC)

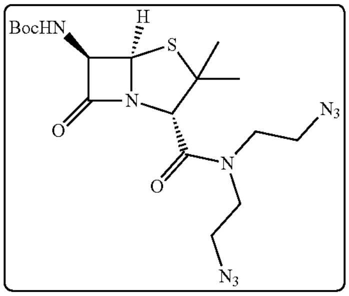

-continued (ID)

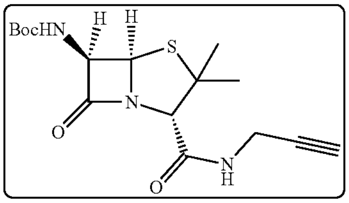

(IE)

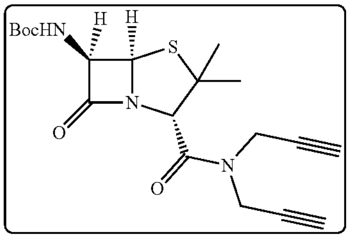

.

3. The process according to claim 1, wherein the deprotection reaction is carried out with a quantity of trifluoroacetic acid ranging from 50 to 100 mmoles in a molar ratio with respect to the compound having formula (I).

4. The process according to claim 1, wherein the deprotection reaction is carried out in a polar solvent selected from methylene chloride (DCM), chloroform ($CHCl_3$) or tetrahydrofuran (THF).

5. The process according to claim 1, wherein the polar solvent is selected from methylene chloride (DCM) and chloroform ($CHCl_3$).

6. The process according to claim 1, wherein the saccharide is selected from peracetylated glucose, galactose, hexose, pentose or oligosaccharides with a terminal alkyne group.

7. The process according to claim 1, wherein the saccharide is peracetylated glucose.

8. An amide derivative of 8-hydroxypenillic acid having the general formula (II) of claim 1 having one of the following structural formulae (IIA), (IIB), (IIC), (IID) and (IIE):

(IIA)

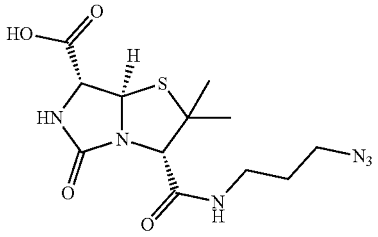

-continued
(IIB)
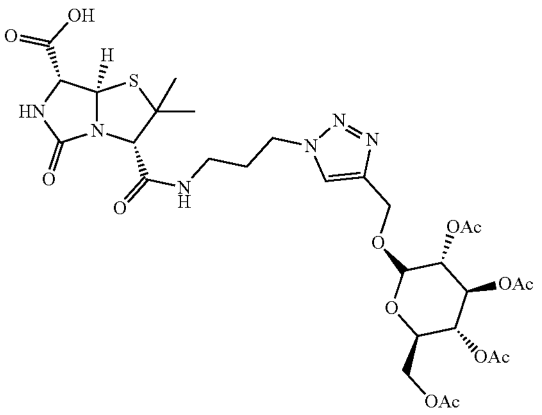
(IIC)
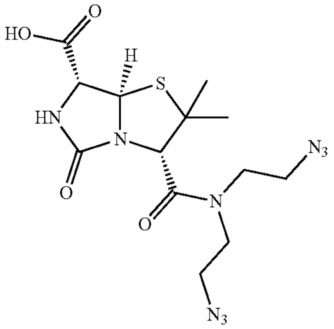
-continued
(IID)
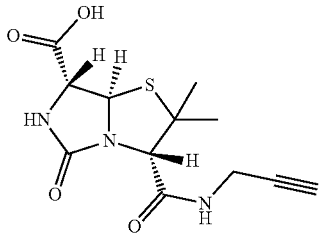
(IIE)
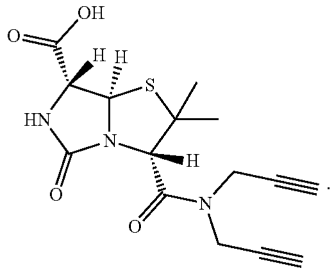
9. The process according to claim 1, wherein the linear alkyl chain, when selected, has from 2 to 3 carbon atoms.
* * * * *